(12) United States Patent
Picart et al.

(10) Patent No.: US 9,249,337 B2
(45) Date of Patent: Feb. 2, 2016

(54) PROCESS FOR PREPARING A SURFACE COATED BY CROSSLINKED POLYELECTROLYTE MULTILAYER FILMS AS A BIOMIMETIC RESERVOIR FOR PROTEINS

(71) Applicants: INSTITUT POLYTECHNIQUE DE GRENOBLE, Grenoble (FR); UNIVERSITE MONTPELLIER 2 SCIENCES ET TECHNIQUES, Montpellier (FR); CENTRE NATIONAL DE LA RECHERCHE SCIENTIFIQUE, Paris (FR)

(72) Inventors: Catherine Picart, Grenoble (FR); Thomas Crouzier, Riom (FR)

(73) Assignees: INSTITUT POLYTECHNIQUE DE GRENOBLE, Grenoble (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 14/310,181

(22) Filed: Jun. 20, 2014

(65) Prior Publication Data
US 2014/0322470 A1 Oct. 30, 2014

Related U.S. Application Data

(62) Division of application No. 13/144,357, filed as application No. PCT/EP2010/050474 on Jan. 15, 2010, now Pat. No. 8,765,179.

(60) Provisional application No. 61/145,158, filed on Jan. 16, 2009.

(51) Int. Cl.
*A61K 9/24* (2006.01)
*C09D 179/02* (2006.01)
*A61L 31/08* (2006.01)
*A61L 31/12* (2006.01)
(Continued)

(52) U.S. Cl.
CPC .............. *C09D 179/02* (2013.01); *A61L 15/28* (2013.01); *A61L 15/32* (2013.01); *A61L 15/44* (2013.01); *A61L 27/20* (2013.01); *A61L 27/227* (2013.01); *A61L 27/34* (2013.01); *A61L 27/54* (2013.01); *A61L 29/085* (2013.01); *A61L 29/16* (2013.01); *A61L 31/08* (2013.01); *A61L 31/10* (2013.01); *A61L 31/12* (2013.01); *A61L 31/16* (2013.01); *A61L 2300/414* (2013.01); *A61L 2420/08* (2013.01); *Y10T 428/1352* (2015.01); *Y10T 428/1393* (2015.01); *Y10T 428/31794* (2015.04)

(58) Field of Classification Search
CPC .............................. A61L 31/08; A61L 31/12
See application file for complete search history.

(56) References Cited

FOREIGN PATENT DOCUMENTS

| EP | 1535952 | 6/2005 |
|---|---|---|
| WO | WO 2006/088368 | 8/2006 |
| WO | WO 2007/132099 | 11/2007 |

OTHER PUBLICATIONS

Written Opinion in International Application No. PCT/EP2010/050474, Dec. 13, 2010, pp. 1-8.

*Primary Examiner* — Carlos Azpuru
(74) *Attorney, Agent, or Firm* — Saliwanchik, Lloyd & Eisenschenk

(57) ABSTRACT

The invention relates to processes for coating a surface with a crosslinked polyelectrolytes multilayer film incorporating a protein, preferably a growth factor type protein. The invention also relates to crosslinked polyelectrolytes multilayer films obtained by this process, and a coated surface obtained therefrom.

3 Claims, 18 Drawing Sheets
(4 of 18 Drawing Sheet(s) Filed in Color)

(51) Int. Cl.
*A61L 15/28* (2006.01)
*A61L 15/32* (2006.01)
*A61L 27/20* (2006.01)
*A61L 27/22* (2006.01)
*A61L 27/34* (2006.01)
*A61L 27/54* (2006.01)
*A61L 29/08* (2006.01)
*A61L 29/16* (2006.01)
*A61L 31/10* (2006.01)
*A61L 31/16* (2006.01)
*A61L 15/44* (2006.01)

PROCESS FOR PREPARING A SURFACE COATED BY CROSSLINKED POLYELECTROLYTE MULTILAYER FILMS AS A BIOMIMETIC RESERVOIR FOR PROTEINS

CROSS-REFERENCE TO RELATED APPLICATIONS

This application is a divisional of U.S. Ser. No. 13/144,357, filed Jul. 13, 2011, now U.S. Pat. No. 8,765,179, which is the U.S. national stage application of International Patent Application No. PCT/EP2010/050474, filed Jan. 15, 2010, which claims the benefit of U.S. Provisional Patent Application No. 61/145,158, filed Jan. 16, 2009.

FIELD OF THE INVENTION

The invention relates to processes for coating a surface with a crosslinked polyelectrolytes multilayer film comprising a protein, preferably a growth factor type protein. The invention also relates to the coated surface obtained by said process.

BACKGROUND OF THE INVENTION

Among the different techniques used to modify surfaces, the deposition of polyelectrolyte multilayers (PEM) has emerged as a very easy handling and versatile tool. Based on the alternate adsorption of polycations and polyanions, this technique allows to buildup films with tunable properties: by adjusting several parameters during buildup such as the chemical nature of the polycations and/or polyanions, pH and ionic strength, immersion and rinsing times, post-treatment of the film, it is possible to obtain an almost infinite variety of architectures. The introduction of electrostatic layer-by-layer (LbL) self-assembly also called electrostatic self-assembly (ESA) has shown broad biotechnology and biomedical applications in thin film coating, micropatterning, nanobioreactors, artificial cells, integrated optics, microelectronic devices, sensors, optical memory devices, encapsulation and drug delivery systems. Indeed, this kind of film is very easy to manufacture.

Of special importance for biomedical applications is the control of the chemical composition of the surface which can affect biological activity. Films made from polypeptides, i.e., poly(L-lysine) and natural polyelectrolytes (e.g., hyaluronan, alginate, chitosan, collagen) allow, for example, biomimetic architectures to be created. Applications include also the fabrication of non adhesive barriers for vascular grafts, the fabrication of films with pro- or anti-coagulant properties or the preparation of hollow capsules for drug release. Bioactivity of the films can be achieved by their functionalization by inserting peptides associated to polyelectrolytes or through the embedding of proteins. For biomaterial applications, biocompatibility is a major requirement: the material or the film covering a material surface must be non-cytotoxic to any living cell and not iatrogenic or allergenic. Another requirement is that the material possesses chemical and physical properties that promote specific cell interactions, either cell adhesion or non-adhesion depending on the final application. In this respect, it was shown that primary cells can be grown on poly(styrenesulfonate)/poly(allyamine hydrochloride) films and on poly(L-lysine)/poly(L-glutamic acid) films for several days while maintaining their phenotype. For instance, Mendelsohn et al., Biomacromolecules, 2003, 4, 96-106, showed that poly(acrylic acid)/poly(allylamine hydrochloride) multilayers can be either non adhesive or adhesive depending on the pH of preparation of the films.

Polyelectrolyte multilayers based on biopolymers or polyaminoacids are hydrogels and must be considered as "soft" and sensitive materials. For example, exposure to solvents, pH and ionic strength jumps can affect their structural integrity and cross-linking constitutes a possible way to stabilize them. Up to now, only few cross-linkable PEM systems have been reported. The approaches generally rely on the cross-linking through condensation reaction of complementary groups located on adjacent layer. Recently, the inventors have described a convenient method to produce crosslinked polyelectrolyte multilayer films which prove to be stabilized with respect to aggressive media, such as solvents, extreme pH, ionic strengths jumps, enzymes and/or phagocytic cells, and can therefore withstand numerous physical, chemical and biological stresses (see EP 1,535,952 and Richert et al. *Biomacromolecules*, 5, 284-294, 2004; Etienne et al. *Biomacromolecules*. 6, 726-733, 2005; Picart et al., *Adv. Funct. Mat.* 15: 1771-1780, 2005).

The controlled delivery of certain proteins from a surface, in particular a biomaterial surface, is an important challenge. This would offer the possibility to concentrate the protein and deliver it locally, thereby also protecting it from degradation by enzymes in tissue fluids. The ability to design surface that can direct cell fate is also an important challenge in the field of tissue engineering and biomaterials. The surface properties of biomaterials often dictate the direct interactions of the material with its environment, in particular cellular interaction. The layer-by-layer (LbL) technique appears to be a convenient strategy for such an application as it allows the precise control of various parameters, such as film architecture, thickness, chemistry, and mechanical properties (Jessel, N. et al. *Adv. Mater.* 2003, 26, 692-695). As the deposition is achieved in aqueous solution, incorporation of sensitive biomolecules such as proteins is possible (Ai, H. et al. *Cell Biochem. Biophys.* 2003, 39, 23-43). It has been shown that proteins adsorbed on top or added as a regular layer in the LbL film retain their activity (Vodouhe, C. et al. *Biomaterials* 2005, 26, 6836-6845).

It is therefore an object of this invention to provide a process for coating a surface with a polyelectrolyte multilayer film incorporating a large amount of proteins, the incorporation rate of proteins being high in comparison with systems available on the market, such as collagen sponges or membranes.

It is a further object of the invention to provide a coated article by a cross-linked polyelectrolyte multilayers film directly obtained by the above mentioned process, said film comprising proteins whose bioactivity remains.

It is a further object of the invention to provide a coated article by a cross-linked polyelectrolyte multilayers film presenting a high concentration of a protein which can be delivered locally, and also protecting it from degradation by enzymes in tissue fluids.

Furthermore, it is an object of the invention to provide a coated article capable of delivering proteins with no burst effect and in particular as a slow release system, and more specifically wherein cells can adhere and differentiate in the case where proteins are growth factors.

The inventors have now discovered that cross-linked polyelectrolyte multilayers film obtained by a coupling agent, such as 1-ethyl-3-(3-dimethylaminopropyl) carbodiimide (EDC), and optionally in the presence of N-hydroxysuccinimide compounds, and subsequently treated to incorporate therein a protein can be of valuable interest and presents several advantages.

SUMMARY OF THE INVENTION

In view of the above, an object of this invention is a process for coating a surface, comprising (a) sequentially depositing on a surface at least one layer of alternate adsorbed polyelectrolytes to provide a coated surface presenting complementary amino and carboxylic reactive groups, wherein a first (or conversely second) polyelectrolyte is a cationic polymer and a second (or conversely first) polyelectrolyte is an anionic polymer, (b) reacting said complementary reactive groups of the coated surface in the presence of a coupling agent, as to form amide bonds between said complementary reactive groups giving rise to a cross-linked polyelectrolyte multilayers film, and (c) treating said cross-linked polyelectrolyte multilayers film with a protein containing solution, preferably with a growth factor type protein containing solution, as to incorporate said protein on and inside said cross-linked polyelectrolyte multilayers film.

Furthermore, the invention relates to a coated article obtained by the process of the present invention.

The cross-linking procedure according to the invention presents the advantage of being very efficient on various types of polyelectrolyte films, whatever the nature of polyelectrolyte is, and whatever the film thickness is (for instance, from few nanometers to dozens of micrometers).

Furthermore, the films can sustain the conditions for a very efficient incorporation of proteins. The obtained films loaded with proteins are capable of delivering proteins with no burst effect and in particular as an efficient slow release system.

Moreover, the bioactivity of incorporated proteins remains, whereas some proteins are known to be degraded under other conditions. The rhBMP-2 loaded films of the invention demonstrate for instance a persistent bioactivity, at least for 10 days, which is a key issue as rhBMP-2 in solution is known to be degraded in few hours.

Finally, the coated article according to the invention is capable of delivering proteins with no burst effect and can be used as an efficient slow release system.

DETAILED DESCRIPTION OF THE INVENTION

The present invention relates to a process for coating a surface, comprising the following steps:

(a) sequentially depositing on a surface at least one layer of alternate adsorbed polyelectrolytes to provide a coated surface presenting complementary amino and carboxylic reactive groups, wherein a first (or conversely second) polyelectrolyte is a cationic polymer comprising said amino groups and a second (or conversely first) polyelectrolyte is an anionic polymer comprising said carboxylic groups, (b) reacting said polyelectrolytes in the presence of a coupling agent, as to form amide bonds between said complementary reactive groups giving rise to a cross-linked polyelectrolyte multilayers film, and (c) treating said cross-linked polyelectrolyte multilayers film with a protein containing solution, preferably with a growth factor type protein containing solution, as to incorporate said protein on and inside said cross-linked polyelectrolyte multilayers film.

The polyelectrolyte multilayers films are more preferably biocompatible. In particular, such biocompatible films can render any coated surface biocompatible. Consequently, such biocompatible materials when applied to biological tissues, in particular within the body, present the advantage of not irritating the surrounding tissues, not provoking an abnormal inflammatory response and not inciting allergic or immunological reaction.

The polyelectrolyte multilayers formed through the process of the present invention comprise at least two or more layers of polyelectrolytes, each further layer having the opposite charge of the previous layer. The film architecture is precisely designed and can be controlled to 1 nm precision with a range from 1 to 50 000 nm, preferably from 100 nm to 30 µm and with a definite knowledge of its molecular composition.

The number of layer pairs in polyelectrolyte multilayers film prepared through the process of the present invention can vary in a wide range and depend on the desired thickness. In particular, the number of layer pairs can vary from 5 to 2000, preferably from 5 to 1000, more preferably from 5 to 100. When a thick polyelectrolyte film is desired, the number of layer pairs can vary from 15 to 1000, preferably from 20 to 500 (in particular from 20 to 60).

As stated above, the thickness of the film can generally vary from 1 nm to 50 000 nm. A film is considered as a thick film when its thickness is more than 300 nm. According to the invention and in a particular embodiment, the thickness of the film is from 500 nm to 20 µm, more preferably from 1 to 10 µm.

The complementary functional groups that can be covalently coupled using an external coupling agent are amino and carboxylic groups of the polyelectrolytes. In particular, the amino groups can be present in the form of hydroxylamine, hydrazide and amine functions. In particular, the carboxylic groups can be present in the form of acids, acid halide (preferably, acid chloride), acid anhydride or activated esters, such as N-hydroxysulfosuccinimide ester or n-paranitrophenyl ester.

The complementary functional groups are covalently bond to the used polymers.

In the present invention, the terms "anionic polymer" relate to a polymer comprising at least one group susceptible to bear a negative charge. The terms "cationic polymer" relate to a polymer comprising at least one group susceptible to bear a positive charge.

Any anionic polymer comprising carboxylic groups can be used in the present invention, including, without limitation thereto, poly(acrylic) acid, poly(methacrylic) acid, poly(glutamic) acid, polyuronic acid (alginic, galacturonic, glucuronic), glycosaminoglycans (hyaluronic acid or a salt thereof (such as sodium)—also called hyaluronan-, dermatan sulphate, chondroitin sulphate, heparin, heparan sulphate, and keratan sulphate), poly(aspartic acid), any combination of the polyamino-acids (in the D and/or L forms), and mixtures thereof.

Any cationic polymer comprising amino groups can be used in the present invention, including, without limitation thereto, poly(lysine), such as poly(D,L-lysine), poly(diallydimethylammonium chloride), poly(allylamine), poly(ethylene)imine, chitosan, polyarginine, such as Poly(L-arginine), Poly(ornithine), polyhistidine, such as Poly(D,L-histidine), poly(mannosamine), and more generally any combination of the polyamino acids (in the D and/or L forms), and mixtures thereof.

In a particular aspect of the invention, the cationic polymer comprising amino group is poly(L-lysine) (or PLL) or the anionic polymer comprising amino group is the hyaluronic acid or a salt hereof, such as hyaluronan sodium (also called generally HA), or heparin (HEP), or a mixture thereof. The polyelectrolyte multilayers film is more preferably a PLL/HA film, a PLL/HEP film or a PLL/mixture of HA and HEP (PLL/HA-HEP) film.

The molecular weight of the polymers identified above can vary in a wide range. More preferably, the molecular weight is in the range from 0.5 kDa to 20,000 kDa, even more preferably, the molecular weight is in the range from 5 to 2,000 kDa.

Polyelectrolyte multilayers films of the invention loaded with a protein are of particular interest, since they act as biomimetic reservoirs for the storage and release of the protein. For instance, the controlled delivery of growth factor from a biomaterial surface can be achieved under very satisfying conditions as it allows to conveniently concentrate the growth factor and to release it locally, and protecting it from degradation of enzymes in tissue fluids, in particular proteases.

Among the growth factor proteins that may be used in the present invention, can be cited in particular those that are useful for therapeutic applications.

As examples of growth factors that may be incorporated in films according to the invention are bone morphogenetic proteins (BMPs), epidermal growth factors (EGF), erythropoietin (EPO), fibroblast growth factor (FGF), granulocyte-colony stimulating factor (G-CSF), granulocyte-macrophage colony stimulating factor (GM-CSF), growth differentiation factor-9 (GDF9), hepatocyte growth factor (HGF), hepatoma derived growth factor (HDGF), insulin-like growth factor (IGF), myostatin (GDF-8), nerve growth factor (NGF) and other neurotrophins, platelet-derived growth factor (PDGF), thrombopoietin (TPO), transforming growth factors, stromal cell-derived factor-1 (SDF-1) and vascular endothelial growth factor (VEGF).

Among the growth factor proteins, the transforming growth factor (TGF) family is a category of choice as this family plays an essential role, e.g., in bone formation through the regulation of osteoprogenitor and osteoblast proliferation and differentiation. Bone morphogenetic protein 2 (BMP-2), a member of the TGF family, stimulates in particular the differentiation of myoblast cells toward an osteoblastic lineage; and its recombinant human form rhBMP-2 is more effective when delivered associated with a biological material such as a polymer.

In a particular aspect of the invention the protein incorporated in the cross-linked polyelectrolyte multilayers film at step (c) of the process of the invention is a growth factor type protein, and preferably a transforming growth factor. More particularly, the growth factor is the bone morphogenetic protein 2 (BMP2) or the stromal cell-derived factor-1 (SDF-1), and more preferably human (hBMP2 or hSDF-1).

The growth factor can be prepared by various methods, including biological or chemical methods. The recombinant form is a particular embodiment. When it is a human recombinant form, it is also called herein rhBMP-2 or rhSDF-1. The chemical method implements generally automated peptide synthesizer. For instance, wild type SDF-1 can be synthesized by the Merrifield solid-phase method on a fully automated peptide synthesizer using fluorenylmethyloxycarbonyl (Fmoc) chemistry.

Films incorporating a protein, in particular a growth factor, according to the invention may be used for therapeutic applications, for instance in the treatment of hematologic, oncologic, inflammatory, immunologic or cardiovascular diseases, or in orthopaedic surgery.

As mentioned before, according to the invention, the process allows having a high incorporation rate of proteins in the films. Said amount will vary upon the protein to be incorporated, its bioactivity and its desired biological or pharmaceutical effect. More specifically, the amount of BMP2 obtained in the film according to the present process can vary from 50 ng/cm$^2$ to 20 μg/cm$^2$, preferably from 0.2 μg/cm$^2$ to 10 μg/cm$^2$, and even more preferably from 1 μg/cm$^2$ to 6 μg/cm$^2$.

As further example, the amount of SDF-1 obtained in the film according to the present process can vary from 50 ng/cm$^2$ to 20 μg/cm$^2$, preferably from 0.2 μg/cm$^2$ to 10 μg/cm$^2$, and even more preferably from 0.3 μg/cm$^2$ to 6 μg/cm$^2$. The concentration of proteins in the solution of step (c) depends on the desired amount of proteins incorporated on and inside the films and can be readily established by one of ordinary skill in the art under experimental routine. For instance, the concentration of BMP2 in the growth factor containing solution is such that the amount of BMP2 incorporated in the film, obtained after step (c), varies from 50 ng/cm$^2$ to 20 μg/cm$^2$, preferably from 0.2 μg/cm$^2$ to 10 μg/cm$^2$, and even more preferably from 1 μg/cm$^2$ to 6 μg/cm$^2$. As further example, the concentration of SDF-1 in the growth factor containing solution is such that the amount of SDF-1 incorporated in the film, obtained after step (c), varies from 50 ng/cm$^2$ to 20 μg/cm$^2$, preferably from 0.2 μg/cm$^2$ to 10 μg/cm$^2$, and even more preferably from 0.3 μg/cm$^2$ to 6 μg/cm$^2$.

The protein loaded crosslinked polyelectrolyte multilayers films obtained according to the invention are particularly useful when they are in contact with various cell types, such as myoblasts and osteoblasts, the cells can adhere, proliferate and optionally differentiate in a very efficient manner.

The coupling agent is an entity, preferably a chemical entity, which enables the formation of amide bonds (or derivatives thereof) between the carboxylic and amino groups of the polyelectrolyte multilayers. The coupling agent can act as a catalyst, which can be removed thereafter, or as a reactant, which creates a spacer (or a link) between the formed amide bonds.

In contrast to conventional agents, such as glutaraldehyde, carbodiimides do not remain as a part of the linkage but simply change to water soluble urea derivatives that present very low cytotoxicity. The films can be preferably thoroughly washed prior to incorporation of the protein as to eliminate traces of urea derivatives.

Moreover, it has been established by the inventors that the cross-linking procedure according to the invention can be carried out on different types of polyelectrolytes, as long as carboxylic groups and amine groups are present in said polyelectrolytes.

The coupling agents are preferably water soluble compounds.

In a particular aspect of the invention, the coupling agent is a carbodiimide compound.

The carbodiimide compounds are preferably compounds of formula (I):

$$RN=C=NR' \qquad (I)$$

wherein R and R', which are identical or different, represent an alkyl or aryl group, preferentially an C1-C8 alkyl group.

The alkyl groups may be linear, cyclic or branched, they can be interrupted by heteroatoms, such S, N or O. In particular, they can be substituted by an amine group, such as for example —N$^+$H(CH$_3$)$_2$. Examples of alkyl groups having from 1 to 8 carbon atoms inclusive are methyl, ethyl, propyl, isopropyl, t-butyl, isobutyl, n-butyl, pentyl, isopentyl, hexyl, heptyl, octyl, 2-ethylhexyl, 2-methylbutyl, 2-methylpentyl, 1-methylhexyl, 3-methylheptyl and the other isomeric forms thereof. Preferably, the alkyl groups have from 1 to 6 carbon atoms.

The aryl groups are mono-, bi- or tri-cyclic aromatic hydrocarbon systems, preferably monocyclic or bicyclic aromatic hydrocarbons containing from 6 to 18 carbon atoms, even more preferably 6 carbon atoms. Examples include phenyl, naphthyl and biphenyl groups.

The carbodiimide compounds are preferably water soluble compounds.

In particular, the carbodiimide compound is 1-ethyl-3-(3-dimethylaminopropyl) carbodiimide (EDC).

The amount of coupling agent can vary on a wide range and depend on the desired degree of crosslinking. In general, said amount is from 5 mM to 1.2 M, preferably from 125 mM to 600 mM and more preferably from 150 mM to 250 mM.

The reaction of carboxylic groups and amino groups of the polyelectrolyte multilayers in the presence of coupling agents, in particular carbodiimide compounds (more particularly EDC), is advantageously carried out also in the presence of N-hydroxysuccinimide compounds.

The N-hydroxysuccinimide compound is preferably N-hydroxysulfo succinimide, more preferably N-hydroxysulfo succinimide para-nitrophenol, or dimethylaminopyridine.

The amount of N-hydroxysuccinimide compound can vary on a wide range. Generally, said amount is from 10 mM to 50 mM. The molar ratio coupling agent/N-hydroxysuccinimide compound is generally from 2 to 20.

The step (b) of the process of the invention involves the reaction of carboxylic groups and amino groups of the polymers in the presence of a coupling agent, preferably carbodiimide compounds, is preferably performed in a water soluble solution, more preferably in an aqueous solution or in any kind of solvent, organic or inorganic. The aqueous solution is advantageously a salt free solution or an aqueous solution containing salts, such KCl, NaCl, or any kind of buffer such as Mes, Tris, Hepes, or phosphate buffers.

Said step (b) is preferably carried out at a pH ranging from 2 to 9, more preferably from 2 to 7.5.

The step (b) reaction can be performed over a large range of temperature from 1° C. to 50° C., preferably from 4° C. to 37° C., more preferably at 6° C.

The degree of crosslinking can also be controlled by varying the concentration of the coupling agent in the solution, preferably the degree of crosslinking obtained through step (b) of the process of the invention is about 50% of the initial carboxylic groups present in the polyelectrolyte.

The time to implement step (b), and more specifically as to obtain a crosslinked polyelectrolyte film, can vary from a wide range. Preferably, the reaction time is from 1 to 24 hours, more preferably from 2 to 18 hours, and even more preferably from 3 to 15 hours.

The step (c) of the process of the invention is preferably carried out at a pH ranging from 2 to 9, more preferably from 2 to 4.5, even more preferably at 3.

The protein containing solution is preferably a buffer, such as Mes, Tris, Hepes, NaCl, KCl, phosphate buffers or a mixture thereof, preferably a solution with a low ionic strength, more preferably a buffer without any salt, such as HCl (for instance HCl at 1 mM).

The time to implement step (c), and more specifically as to incorporate said protein on and inside said cross-linked polyelectrolyte multilayers film, can vary from a wide range. Preferably, the treating time of step (c) is from 30 min to 24 hours, preferentially from 1 hour to 18 hours and more preferably from 2 hours to 12 hours.

Another aspect of the present invention relates to the cross-linked polyelectrolyte multilayers films directly obtained by any one of the above described processes.

Another aspect of the present invention relates to an article coated according to a process of the present invention. Suitable articles supporting the layer elements according to the invention are those having a surface which is preferably accessible to solvents, for example flat, cylindrical, conical, spherical or other surfaces of uniform or irregular shape. It can also include interior surfaces of bottles, tubings, beads, sponges, porous matrices and the like. The substrate material may be of any type such as glass and bioactive glass, plastic, metals (such as titanium or others), alloys (such as stainless steel or nickel titanium), polymers, ceramic (such as hydroxyapatite, tricalcium phosphate or mixtures thereof, commercialized for instance as BCP BiCalPhos by Medtronics or as TRIHA+ by Teknimed), biological tissue and more widely, any type of porous or non porous material.

In a particular aspect, the coated article according to the invention is rendered or is maintained biocompatible.

In certain embodiments, an article coated by the method of the present invention is selected from the group consisting of blood vessel stents, tubing, angioplasty balloons, vascular graft tubing, prosthetic blood vessels, vascular shunts, heart valves, artificial heart components, pacemakers, pacemaker electrodes, pacemaker leads, ventricular assist devices, contact lenses, intraocular lenses, sponges for tissue engineering, foams for tissue engineering, matrices for tissue engineering, scaffolds for tissue engineering, biomedical membranes, dialysis membranes, cell-encapsulating membranes, drug delivery reservoirs, drug delivery matrices, drug delivery pumps, catheters, tubing, cosmetic surgery prostheses, dental prostheses, bone and dental implants, wound dressings, sutures, soft tissue repair meshes, percutaneous devices, diagnostic biosensors, cellular arrays, cellular networks, microfluidic devices, and protein arrays.

According to another embodiment, the article according to the invention is a material used in the orthopaedic surgery, such as orthopaedic prostheses, bone grafts or bone substitutes.

The surface to be coated can be at least a portion of a surface of the article such as defined above.

Sequentially depositing on a surface alternating layers of polyelectrolytes may be accomplished in a number of ways. The depositing process generally involves coating and optionally rinsing steps.

The process includes all possibilities for bringing into contact a liquid containing either a polymer or an active agent with the surface on which the film is being assembled. Step (a) usually comprises sequentially bringing a surface into contact with polyelectrolyte solutions thereby adsorbing alternated layers of polyelectrolytes to provide a coated surface presenting amino and carboxylic groups. Classic methods comprise dipping, dip-coating, rinsing, dip-rinsing, spraying, inkjet printing, stamping, printing, microcontact printing, wiping, doctor blading or spin coating. Another coating process embodiment involves solely spray-coating and spray-rinsing steps. However, a number of alternatives involve various combinations of spray- and dip-coating and rinsing steps. These methods may be designed by a person having ordinary skill in the art.

One dip-coating alternative involves, during the step (a) of the process of the present invention, the steps of applying a coating of a first polyelectrolyte to a surface by immersing said surface in a first solution of a first polyelectrolyte; rinsing the surface by immersing the surface in a rinsing solution; and, optionally, drying said surface. This procedure is then repeated using a second polyelectrolyte, with the second polyelectrolyte having charges opposite of the charges of the first polyelectrolyte, in order to form a polyelectrolyte pair of layers.

The immersion time for each of the coating and rinsing steps as defined above may vary depending on a number of factors. Preferably, contact times of the surface into the polyelectrolyte solution occurs over a period of about 1 second to 30 minutes, more preferably about 1 to 20 minutes, and most preferably about 1 to 15 minutes. Rinsing may be accomplished in one step, but a plurality of rinsing steps has been found to be quite efficient. Rinsing in a series of about 2 to 5 steps is preferred, with contact times with the rinsing solution preferably consuming about 1 to about 6 minutes.

Another embodiment of the coating process involves a series of spray coating techniques. The process generally includes the steps of applying a coating of a first polyelectrolyte to a surface by contacting the surface with a first solution of a first polyelectrolyte; rinsing the surface by spraying the surface with a rinsing solution; and, optionally, drying the surface. Similar to the dip-coating process, the spray-coating process may then be repeated with a second polyelectrolyte, with the second polyelectrolyte having charges opposite of the charges of the first polyelectrolyte.

The contacting of surface with solution, either polyelectrolyte or rinsing solution, may occur by a variety of methods. For example, the surface may be dipped into both solutions. One preferred alternative is to apply the solutions in a spray or mist form. Of course, various combinations may be envisioned, e.g., dipping the surface in the polyelectrolyte followed by spraying the rinsing solution.

The spray coating application may be accomplished via a number of methods known in the art. For example, a conventional spray coating arrangement may be used, i.e., the liquid material is sprayed by application of fluid, which may or may not be at elevated pressure, through a reduced diameter nozzle which is directed towards the deposition target.

Another spray coating technique involves the use of ultrasonic energy or electrostatic spray coating in which a charge is conveyed to the fluid or droplets to increase the efficiency of coating. A further method of atomizing liquid for spray coating involves purely mechanical energy. Still another method of producing microdroplets for spray coatings involves the use of piezoelectric elements to atomize the liquid.

Some of the previously-described techniques may be used with air assist or elevated solution pressure. In addition, a combination of two or more techniques may prove more useful with some materials and conditions.

A person having ordinary skill in the art will be able to select one or more coating methods without undue experimentation given the extensive teachings provided herein.

According to the present invention, the coating steps of the depositing process implement cationic and anionic polyelectrolytes as defined above.

Suitable solvents for polyelectrolyte solutions and rinsing solutions are: water, aqueous solutions of salts (for example NaCl, $MnCl_2$, $(NH_4)_2SO_4$), any type of physiological buffer (Hepes, phosphate buffer, culture medium such as minimum essential medium, Mes-Tris buffer) and water-miscible, non-ionic solvents, such as C1-C4-alkanols, C3-C6-ketones including cyclohexanone, tetrahydrofuran, dioxane, dimethyl sulphoxide, ethylene glycol, propylene glycol and oligomers of ethylene glycol and propylene glycol and ethers thereof and open-chain and cyclic amides, such as dimethylformamide, dimethylacetamide, N-methylpyrrolidone and others. Polar, water-immiscible solvents, such as chloroform or methylene chloride, which can contain a portion of the abovementioned organic solvents, insofar as they are miscible with them, will only be considered in special cases. Water or solvent mixtures, one component of which is water, are preferably used. If permitted by the solubility of the polyelectrolytes implemented, only water is used as the solvent, since this simplifies the process.

In particular embodiments, films prepared according to the process of the invention are polyelectrolyte multilayers films, preferably PLL/HA, PLL/HEP or PLL/HA-HEP films, cross-linked at levels higher than 30 mg/mL of EDC which allowed a long term differentiation of myoblast cells. Myoblast cells hence differentiate into myotubes, which is the regular differentiation pathway for these myoblast cells, in particular the C2C12 myoblast cells.

For the PLL/HA films prepared according to the process of the present invention wherein step (c) is performed with a rhBMP2 containing solution, the concentration of rhBMP2 in the solution is ranging from 0.5 to 150, preferably from 5 to 50 µg/mL, even more preferably from 10 to 30 µg/mL, and more particularly is of 20 µg/mL. For these PLL/HA films, the absorbed amount of rhBMP2 is optimized with a pH ranging from 1 to 6, preferably from 2 to 5, and more preferably of 3. The ionic strength of the solution also affects the solubility of the rhBMP2 and is ranging from 0 to 250 mM of NaCl, preferably from 0 to 100 mM, and more preferably from 0 to 50 mM.

Homogeneous PLL/HA loaded rhBMP2 films were obtained carrying out the step (c) of the process of the invention with a solution free of salts, and more preferably at pH=3.

The PLL/HA loaded rhBMP2 films obtained through the process of the present invention exhibit a particularly strong affinity of the rhBMP2 protein for HA versus PLL.

For the PLL/HA films prepared according to the process of the present invention wherein step (c) is performed with a SDF-1 containing solution, the concentration of SDF-1 in the solution is ranging from 0.5 to 150, preferably from 5 to 50 µg/mL, even more preferably from 10 to 30 µg/mL, and more particularly is of 20 µg/mL. For these PLL/HA films, the absorbed amount of SDF-1 is optimized with a pH ranging from 1 to 6, preferably from 2 to 5, and more preferably of 3. The ionic strength of the solution also affects the solubility of the SDF-1 and is ranging from 0 to 250 mM of NaCl, preferably from 0 to 100 mM, and more preferably from 0 to 50 mM.

Homogeneous PLL/HA loaded SDF-1 films were obtained carrying out the step (c) of the process of the invention with a solution free of salts, and more preferably at pH=3.

The PLL/HA loaded SDF-1 films obtained through the process of the present invention exhibit a particularly strong affinity of the SDF-1 protein for HA versus PLL.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 5A size-exclusion chromatography elution profiles of a mixture of rhBMP-2/HA 1:10 mol/mol (first peak) and of rhBMP-2 alone (second peak) suspended in 40 mM Tris without added salt at PH 7.4.

FIG. 5B size-exclusion chromatography elution profiles of a mixture of rhBMP-2/HA 1:10 mol/mol, suspended in 1 mM HCl without added salt at PH 3. Only one elution peak is observed in the void volume.

Further aspects and advantages of the present invention will be disclosed in the following examples, which should be regarded as illustrative and not limiting the scope of this application. All cited references are incorporated therein by references.

EXAMPLES

1.1 Adsorption of BMP-2 and Initial Release in a Physiological Buffer

Figure 1:
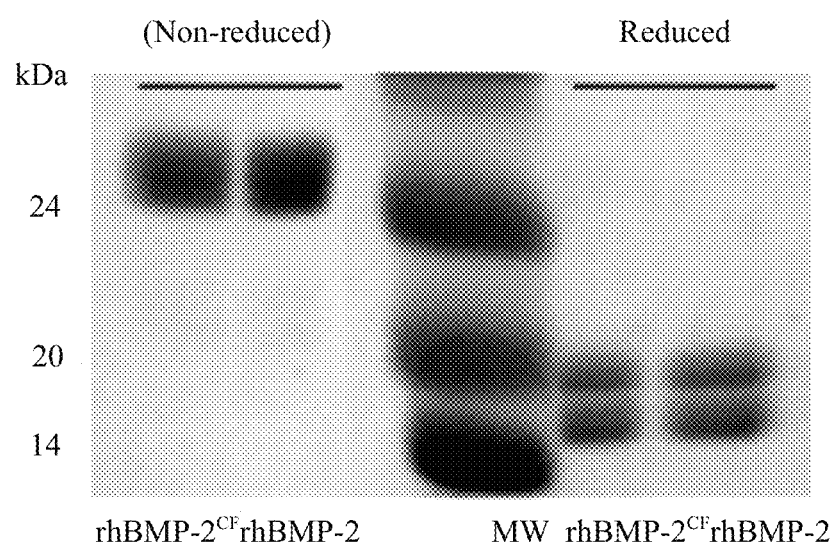
FIG. 1. Gel electrophoresis of fluorescently labelled BMP-2 dimer (first line, BMP-$2^{CF}$) and BMP-2 dimer (second line) prior reduction as well as after reduction by a dithiothreitol solution ($4^{th}$ and $5^{th}$ lines). The MW markers are also indicated (central column).

For this purpose, BMP-2$^{CF}$ (labeled with carboxyfluorescein) was employed and measurements were performed by microfluorimetry in 96 well plates, which allows working with only small amounts of BMP-2 in each well and to screen several conditions in a single experiment. To verify BMP-2's labeling quality BMP-2 and BMP-2$^{CF}$ were submitted to gel electrophoresis (FIG. 1). In non-reducing conditions, both BMP-2 and BMP-2$^{CF}$ were found in the dimeric form (MW of ~27 kDa), which is known to be the active form. In reducing conditions (in the presence of DTT), both BMP-2 and BMP-2$^{CF}$ were dissociated into monomers after gel electrophoresis. Also, exposure of the gel to UV light revealed fluorescence of the BMP-2$^{CF}$ bands. This indicated that the fluorophore grafting onto BMP-2 was successful and did not affect its dimeric structure.

Figures 2A, 2B:
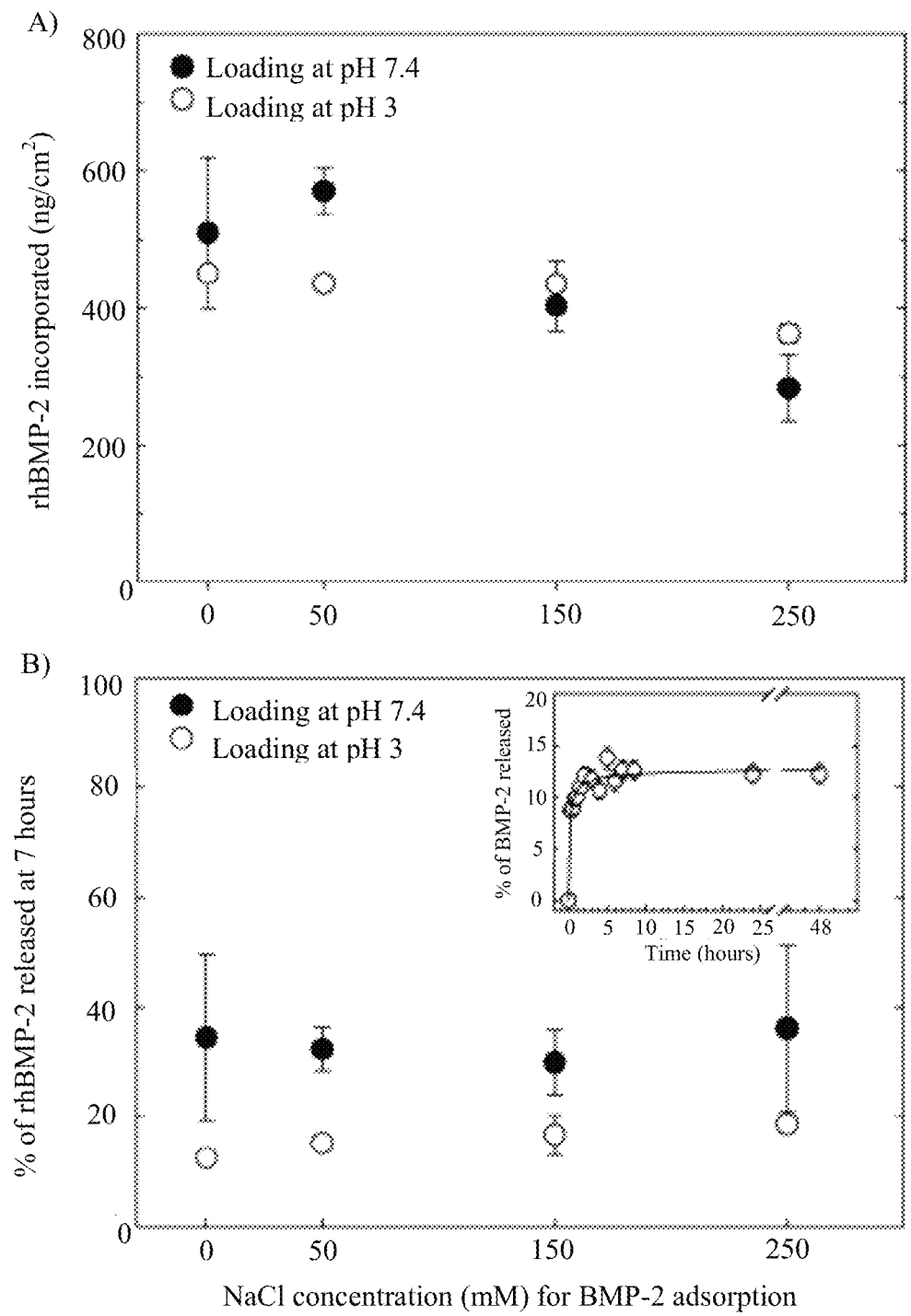
FIGS. 2A-2D. (A) Incorporated amounts of BMP-2 expressed in $ng/cm^2$ and (B) percentage of release of the incorporated amount as a function of pH and ionic strength of the initial BMP-2 solution at 7 h of release, after which a plateau was reached (see inset for release after adsorption in 1 mM HCl without salt). Release was performed in the Hepes-NaCl buffer at pH 7.4. In all cases, BMP-$2^{CF}$ initial solution concentration was 20 µg/ml (C, D) Confocal images showing the difference of BMP-$2^{RHOD}$ layer homogeneity when deposited at pH 3 (C) or at pH 7.4 (Hepes-50 mM NaCl, corresponding to the maximum incorporated amount in FIG. 2A) (D) (image size is 143×143 µm). Images have been acquired in a Hepes-NaCl buffer (pH 7.4, 0.15 M NaCl) after the rinsing steps.
Figure 2C:
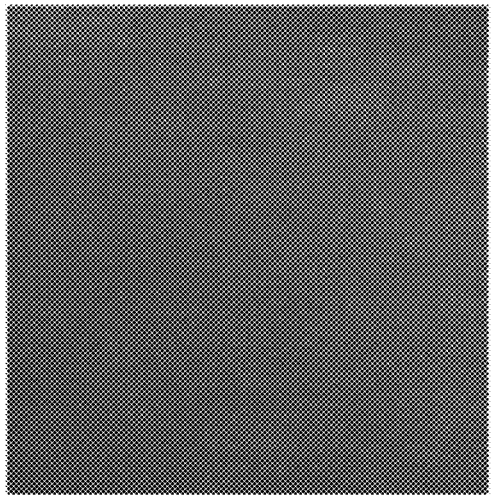
Figure 2D:
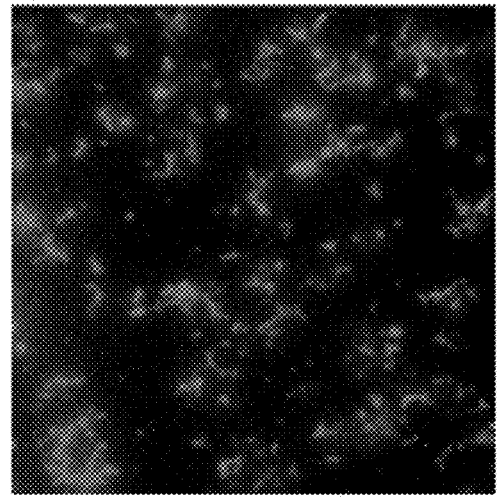

The influence of the cross-linking extent (or EDC concentration) on the differentiation of myoblast into myotubes, which is the regular differentiation pathway for the C2C12 myoblast cells has been examined and the films cross-linked at EDC higher than 50 mg/mL allowed a long term differentiation in myotubes (K. Ren, T. Crouzier, C. Roy, C. Picart. Adv. Funct. Mater. 2008, 18, 1378-1389). Thus, (PLL/HA) films cross-linked at 50 mg/mL were chosen as a reference in the present study as these films allow myoblast adhesion, proliferation and differentiation into myotubes. The experimental conditions for BMP-2 loading in cross-linked (PLL/HA) films were established by quantifying, for a fixed concentration of BMP-2 deposited onto the films (20 μg/mL), how the adsorbed amount varied with pH (for pH 3 and 7.4) and ionic strength (from 0 to 250 mM NaCl), parameters that are known to greatly affect BMP-2 solubility (FIG. 2).

Figure 10:
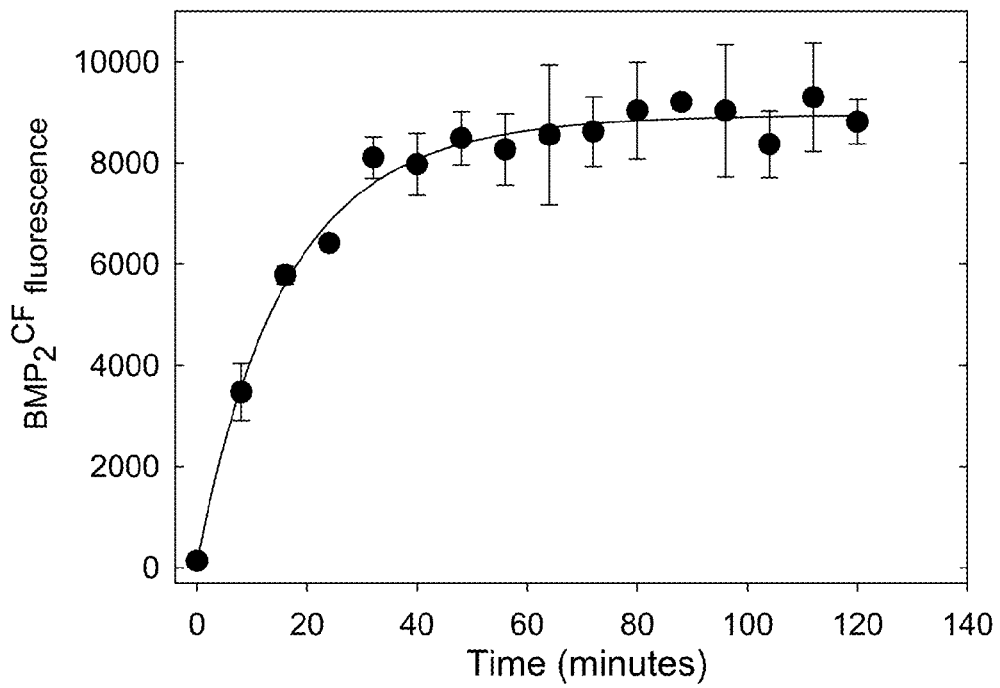
FIG. 10. Kinetics of BMP-2 adsorption on a cross-linked (PLL/HA)$_{12}$ film. A plateau is reached in about 60 min. The initial BMP-2 loading concentration was 20 µg/mL in 1 mM HCl.
Figure 11:
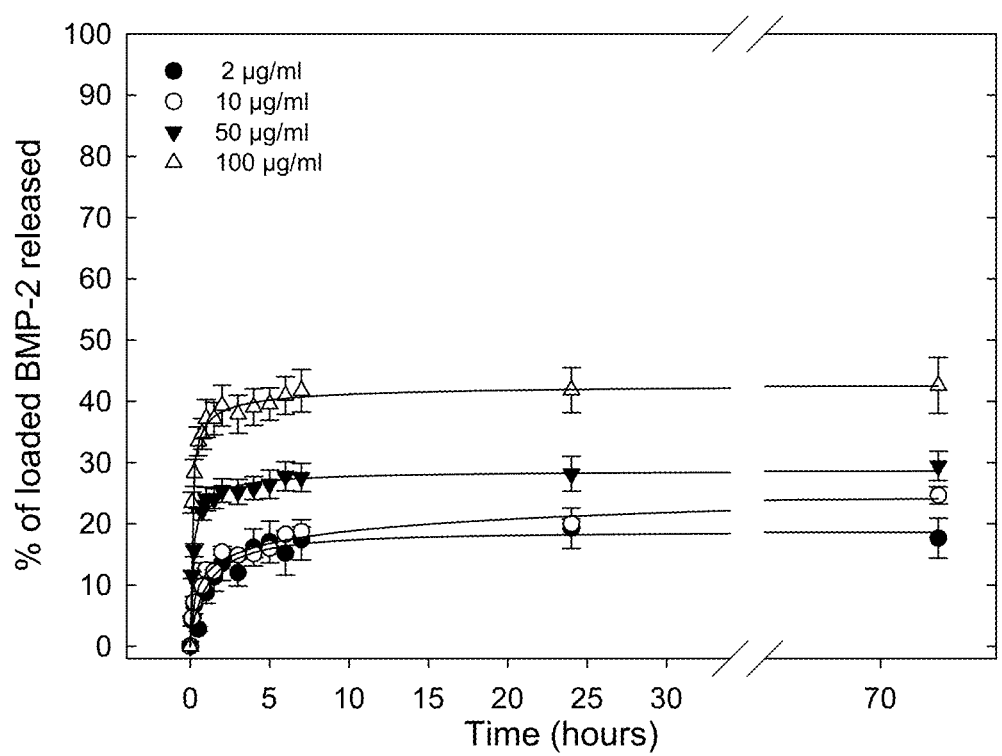
FIG. 11. Time course of BMP-2 cumulative release in Hepes-NaCl buffer (pH 7.4) at increasing initial BMP-2 concentrations (2, 10, 50 and 100 µg/mL). An equilibrium value is reached after about 7 h of release.

Maximum loading was reached in about one hour (FIG. 10), exhibited only minor dependence on pH and decreased with increasing ionic strength. The maximum loading was reached at low ionic strength (below 50 mM NaCl). Release in a physiological buffer was first investigated, as many matrices often exhibit a "burst release" after loading (R. H. Li, J. M. Wozney. Trends Biotechnol. 2001, 19, 255-265). The lowest proportion of material released was obtained when BMP-2 was adsorbed at pH 3 without salt (less than 20% release when the initial BMP-2 concentrations were below 10 μg/mL) (Table 1 below). By using deposition at pH 3 without salt, a more homogeneous layer could be visualized by confocal laser scanning microscopy (CLSM) compared to deposition at pH 7.4 (FIG. 2 C,D). When the film is rinsed with Hepes/NaCl solution at pH 7.4, BMP-2's solubility diminishes drastically which may lead to BMP-2 trapping in the film. Of note, release occurred mostly during the first 5 hours after which a steady state was reached without further loss of BMP-2 for several days and several rinsing steps (FIG. 2 B-inset). For the (PLL/HA) films, the "burst" is thus rather limited from 0-20% for an initial BMP-2 concentration of 10 μg/mL to 44% for higher BMP-2 initial concentrations (Table 1 and FIG. 11). As the films were always thoroughly washed in the physiological buffer prior to being introduced in the culture medium, the BMP-2 quantity remaining in the film after 7 h of release will be taken as the "effective" incorporated amount. These effective incorporated amounts are gathered in Table 1 for (PLL/HA)$_{12}$ films.

Table 1. Summary of BMP-2 loading into cross-linked (PLL/HA)$_{12}$ films (1 μm in thickness). The initial adsorbed amounts were measured by microfluorimetry directly after loading from BMP-2 solutions at different concentrations in 1 mM HCl (pH 3) and release in Hepes-NaCl 0.15 M, pH 7.4. As a plateau in cumulative release was observed after about 7 hours (see FIG. 11), the percentage of BMP-2 released is given at this time. The corresponding "effective" incorporated amount is thus taken as the amount retained in the film after 7 h in the rinsing buffer. The fold increase of the BMP-2 volumic concentration of adsorbed BMP-2 (the volumic concentration in the film being calculated by dividing the adsorbed amount by the film thickness, i.e., 1 μm), as compared to its initial bulk concentration, is also given.

TABLE 1

| BMP-2 initial solution concentration (μg/mL) | 1 | 2 | 5 | 10 | 20 | 50 | 100 | 150 |
|---|---|---|---|---|---|---|---|---|
| Initial adsorbed amounts (ng/cm$^2$) | 28 ± 8 | 121 ± 19 | 318 ± 58 | 480 ± 18 | 782 ± 35 | 975 ± 40 | 1319 ± 28 | 1258 ± 42 |
| % released after 7 h | 9 ± 5 | 17 ± 6 | 20 ± 8 | 19 ± 2 | 20 ± 2 | 28 ± 2 | 42 ± 4 | 44 ± 6 |
| Effective incorporated amount (ng/cm$^2$) | 25 ± 7 | 100 ± 20 | 254 ± 57 | 390 ± 21 | 622 ± 32 | 706 ± 31 | 769 ± 61 | 702 ± 65 |
| Fold increase Volume concentration | 256 | 501 | 507 | 390 | 310 | 141 | 77 | 47 |

Figure 3:
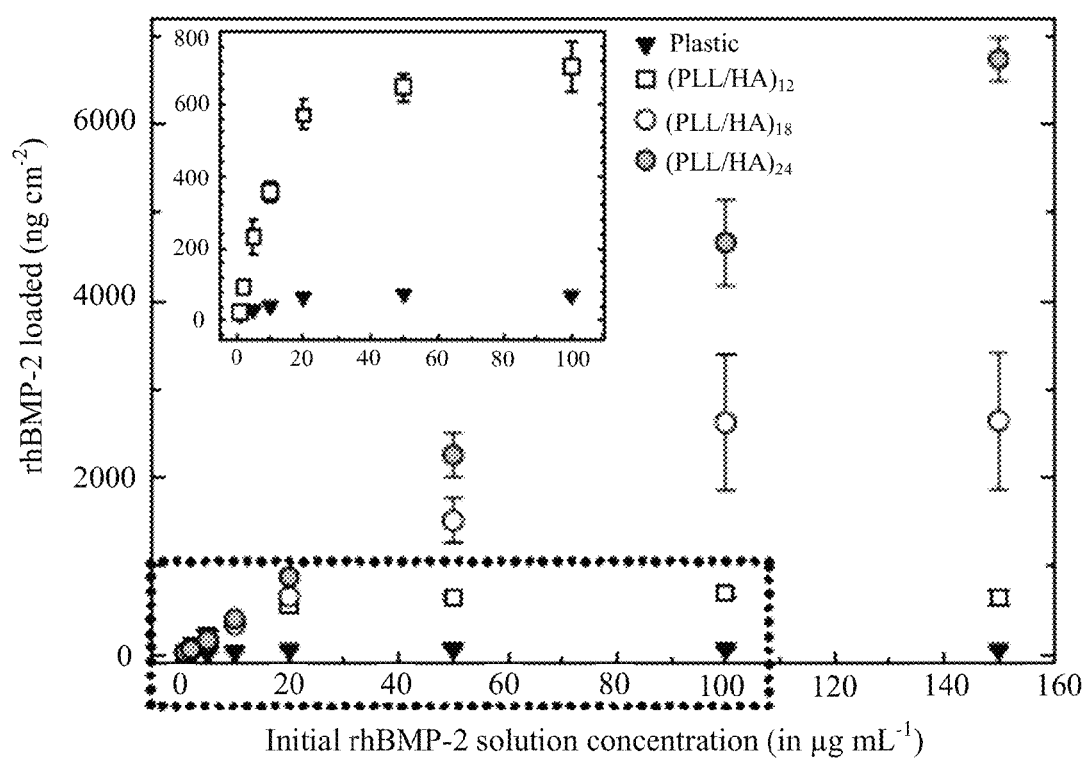
FIG. 3. Amount of BMP-2 loaded in cross-linked (PLL/HA)$_i$ multilayer films of various thicknesses (i=12~1 µm, i=18~1.6 µm, i=24~3.5 µm) as a function of the initial BMP-2 solution concentration. The inset figure is a zoom on the data contained in the rectangular dotted box (i.e., for plastic and for the 12 layer pairs film). 50 µL of BMP-2 solution was deposited per well (surface of the well 0.36 cm$^2$). Plastic is also given as control. Data are means±SD of three samples.

Based on this preliminary study, BMP-2 suspended in 1 mM HCl (pH 3, no added salt) was subsequently used for film loading. Next the film thickness was varied and modulation of the BMP-2 incorporated amount for films of various thicknesses (i.e., containing 12, 18 and 24 layer pairs) and by raising BMP-2 initial concentrations was investigated (FIG. 3). For a given film thickness, the adsorbed amounts were higher when the initial BMP-2$^{CF}$ concentration was raised. But over the range of concentration investigated, the adsorbed amounts leveled off only for the films containing 12 and 18 layer pairs (at respectively 40 μg/mL and 100 μg/mL initial BMP-2 concentrations). It is important to note that BMP-2$^{CF}$ adsorption on control plastic was always negligible compared to the amount adsorbed on (PLL/HA) films, indicating a real reservoir effect of the film.

The amount of BMP-2 present in the films can thus be tuned by varying the BMP-2 initial solution concentration and that amount can be maximized by increasing the film thickness. An advantage of using (PLL/HA) films as a delivery reservoir is to obtain a significantly higher local concentration of BMP-2. This value can indeed be estimated, knowing the incorporated amounts of BMP-2 in (PLL/HA) films and was found to be up to ~500 more concentrated than the corresponding bulk BMP-2 initial concentration (for a 5 µg/mL BMP-2 initial concentration and a film containing 12 layer pairs, 1 µm thick), which is the highest fold increase obtained in the experimental conditions (Table 1). Thus, the growth factor local concentration is drastically raised when it is confined to the film.

1.2. Visualization of Partial Diffusion of BMP-2 in (PLL/HA) Films

Figure 4:
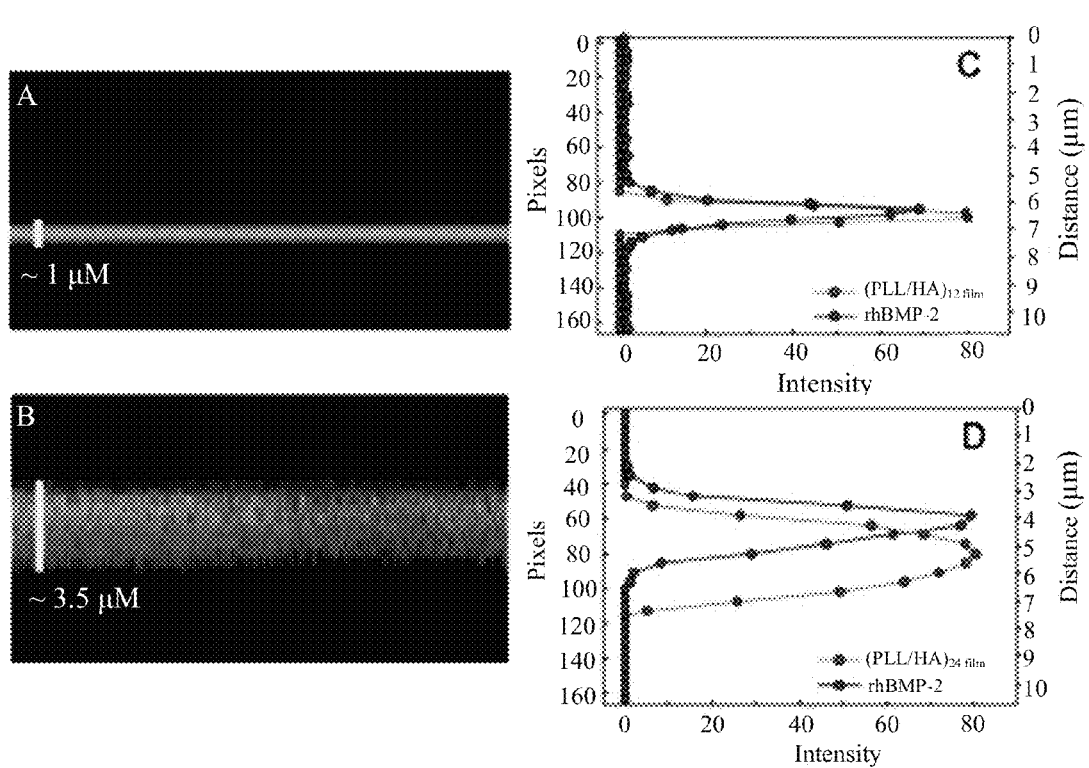
FIGS. 4A-4D. CLSM observations in Hepes-NaCl buffer (pH 7.4) of cross-linked (PLL/HA)$_i$-PLL$^{FITC}$-HA multilayer films loaded with BMP-2. (A) i=12 and (B) i=24. PLL$^{FITC}$ was used to visualize the whole film and BMP-2$^{Rhod}$ was adsorbed at 20 µg/mL (in 1 mM HCl) and rinsed for seven hours in Hepes-NaCl buffer (pH 7.4) before observation. The corresponding z-intensity profiles are given along with the film thickness (left Y axis) for BMP-2$^{Rhod}$ (red) and for PLL$^{FITC}$ (green) (C, D).
Figure 12:
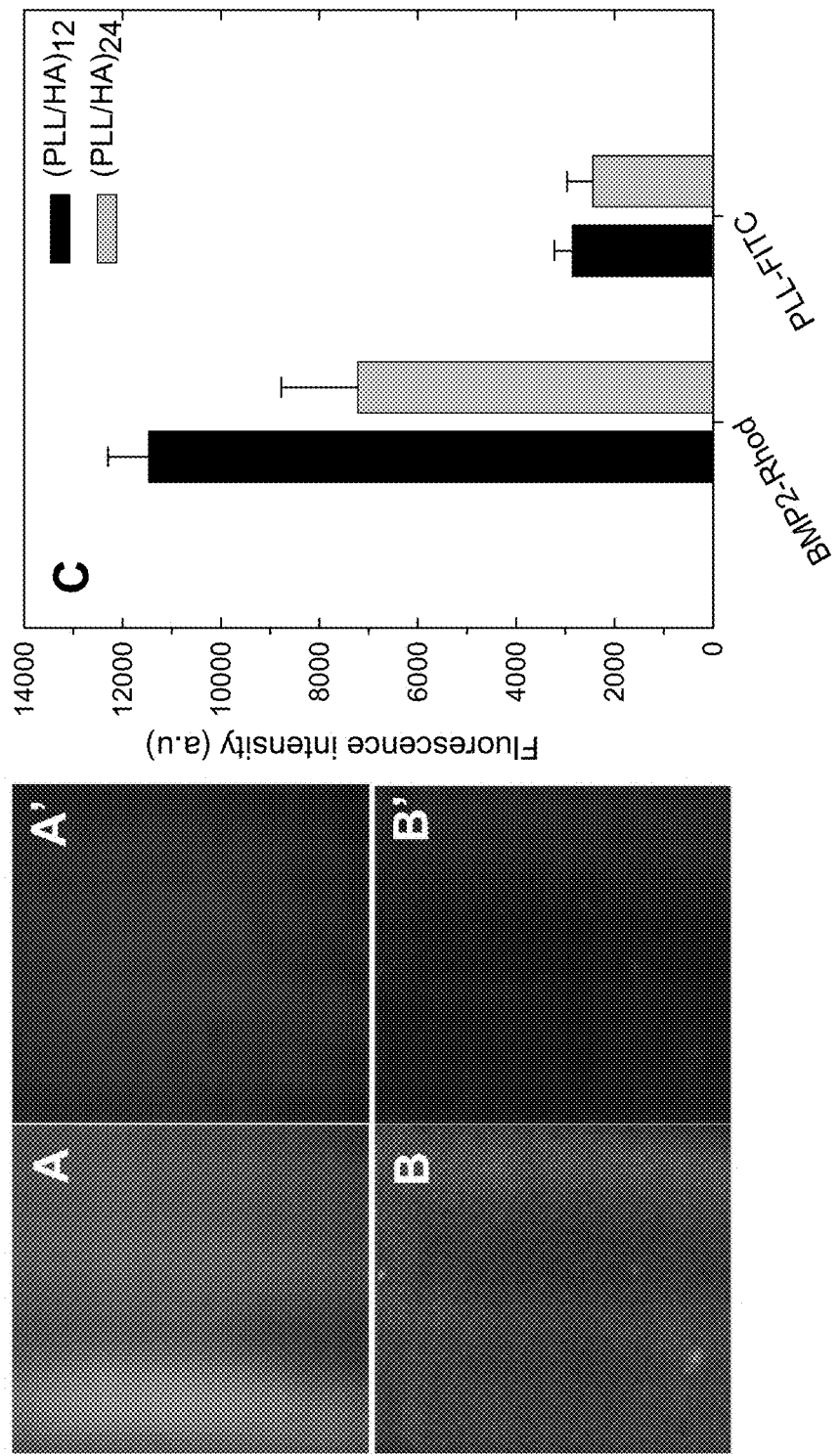
FIGS. 12A-12C. TIRF observations of a (PLL/HA)$_{12}$-PLL$^{FITC}$-HA film (A,A') and of a (PLL/HA)$_{24}$-PLL$^{FITC}$-HA film (B,B') loaded with BMP-2$^{Rhod}$. The observations were performed on an inverted microscope Nikon TE Eclipse FRAP/TIRF equipped with a 100× oil objective (NA 1.4), a Cascade 512B camera and a TIRF3 module at wavelength 491 nm and 546 nm. Film buildup and loading conditions were the same as in FIG. 4. (C) Mean fluorescence over the entire image measured for BMP-2$^{Rhod}$ and PLL$^{FITC}$ for the films. BMP-2$^{Rhod}$ fluorescence appears stronger in the film composed of 12 layer pairs as compared to that containing 24 layer pairs, suggesting that less BMP-2 has diffused down to the glass substrate in the thickest film.

The evolution of the adsorbed amounts with the film thickness given in FIG. 3 indicates that BMP-2 most probably diffuses within the film. In fact, if BMP-2 was simply adsorbed on the film surface, the adsorbed amounts should be independent of the film thickness. A visual and qualitative proof of BMP-2 diffusion in the film was brought from confocal microscopy images. For these experiments, BMP-2 was labeled with rhodamine (BMP-$2^{Rhod}$) and the entire film was visualized by confocal microscopy using PLL$^{FITC}$ thanks to its known diffusion inside the exponentially growing film before crosslinking (FIG. 4). The overlay of the green and red channels for films containing 12 or 24 layer pairs (FIG. 4 A,B) as well as the intensity profiles along the z-direction (FIG. 4 C,D) indicates that BMP-2 diffuses throughout the entire (PLL/HA)$_{12}$ film, leading thus to its homogenous distribution in films containing 12 layer pairs. In thicker films (PLL/HA)$_{24}$, BMP-2 seems to accumulate in the upper part of the film with a limited diffusion within the film. Knowing the z-resolution of these confocal images (~500 nm), it was difficult to assess precisely the thickness over which BMP-2 is diffusing. A further proof of BMP-2 diffusion down to the glass substrate was brought from total internal reflection fluorescence (TIRF) microscopy (FIG. 12). The penetration depth of the evanescent wave being of the order of few hundreds of nanometers above the glass substrate, the visualization of the BMP-$2^{Rhod}$ loaded films by TIRF proves the presence of BMP-2 in the evanescent field. As the BMP-2 dimer is about 7×3×3 nm in size (27 kD), its diffusion also indicates that the pore size of the film is at least 10 nm.

All the subsequent experiments with cells were carried out on cross-linked (PLL/HA)$_{12}$ films as the amounts of BMP-2 inserted in these films (FIG. 3B, inset) were largely sufficient to induce C2C12 myoblast differentiation in osteoblasts.

1.3. Interaction of BMP-2 with HA

Figures 5A, 5B:
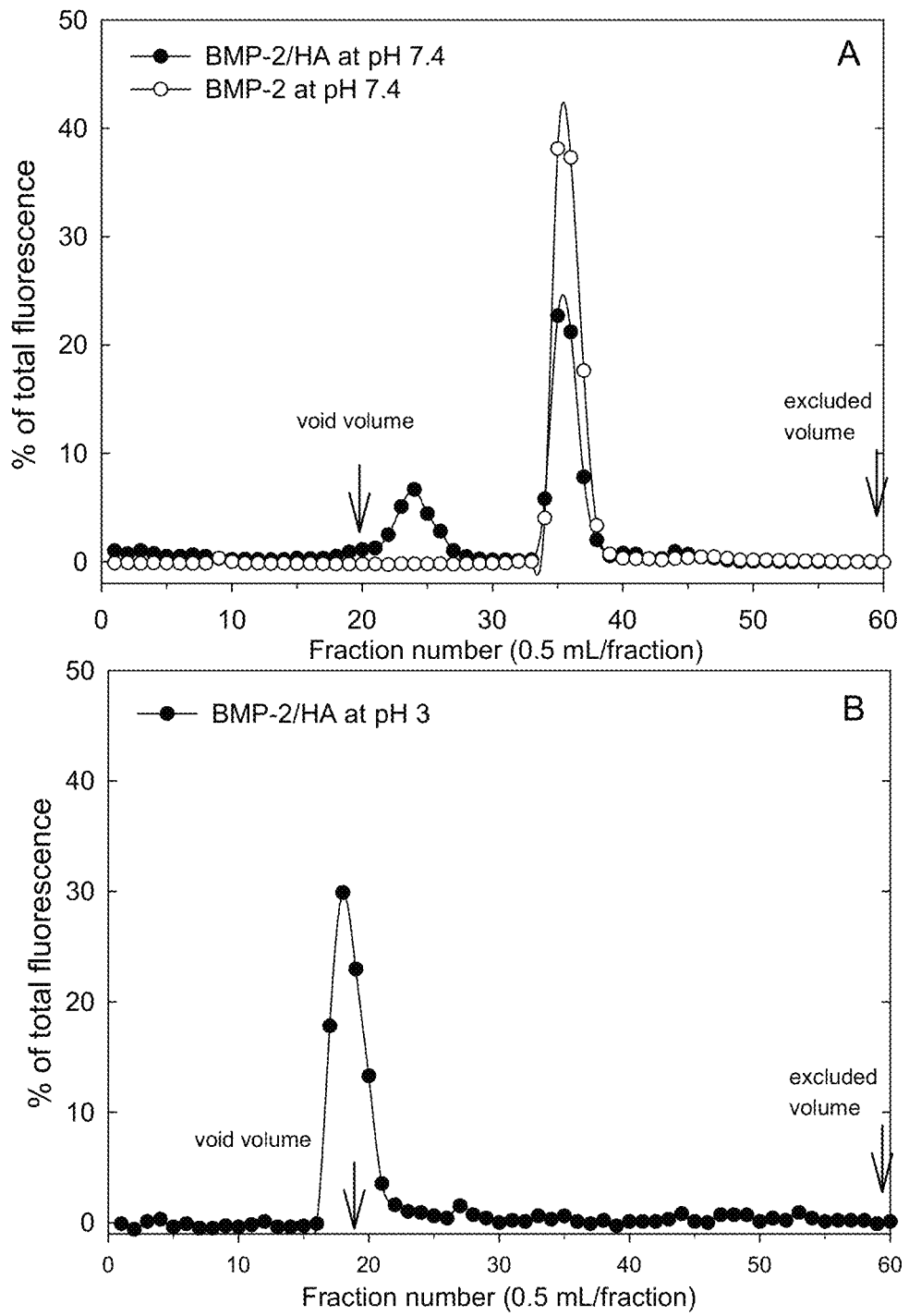
FIGS. 5A-5B. Size exclusion chromatography elution profile of either a mixture of BMP-2$^{CF}$ and HA (~1/10 ratio mol/mol) (first peak) or BMP-2$^{CF}$ alone (second peak) suspended in 1 mM HCl (pH 3 without salt). The results suggest an association of BMP-2 with HA.

A BMP-$2^{CF}$/HA mixture (~1/10 mol/mol) was analyzed by size exclusion chromatography. When elution was performed in 1 mM HCl, all BMP-2 was eluted in the void volume of the column, indicating that it associates with HA. At pH 7.4 (without added salt), a fraction of the BMP-$2^{CF}$, presumably associated with HA, was excluded sooner than the other fraction being recovered in the retention volume expected from the size of BMP-2 (FIG. 5). These data show that BMP-2 binds to hyaluronan (at pH 3 and 7.4) and may provide an explanation for the trapping of BMP-2 within the film. This interaction has not been described previously, although structural interactions of BMP-2 with sulfated polysaccharides, specifically heparin have been previously reported.

1.4. Release of BMP-2 in Culture Medium

Figures 6A, 6B:
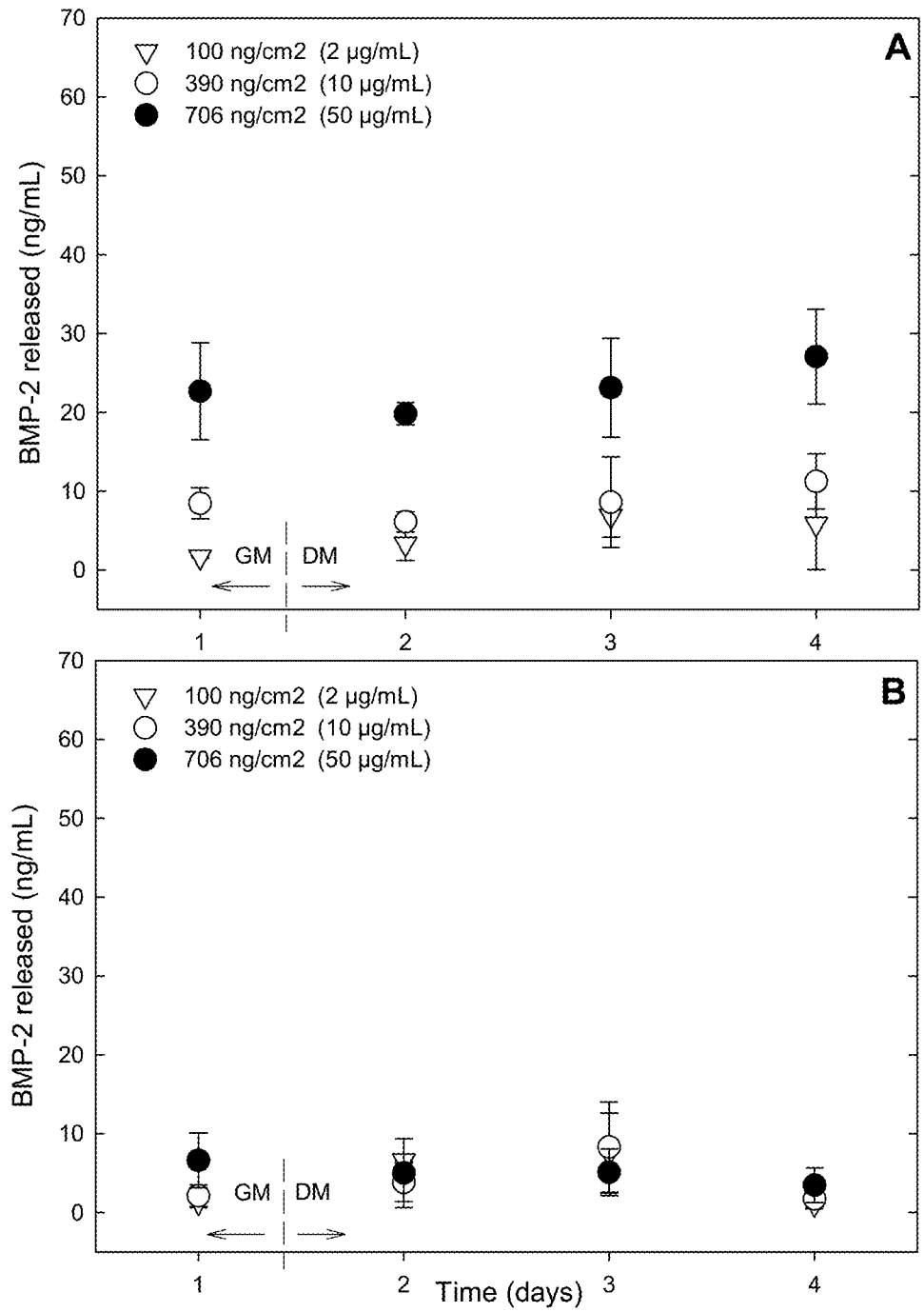
FIGS. 6A-6B. Release of BMP-2 in the culture medium quantified by ELISA. Growth medium (GM) was removed at day 1 and replaced by differentiation medium (DM). The media in contact with the BMP-2 loaded films (at 2, 10, 50 µg/mL initial concentrations, 50 µL per well, surface of the well 0.36 cm$^2$) contained less than 25 ng/ml of BMP-2 for films without cells seeded on the films (A) and less than 10 ng/ml BMP-2 above cultured films (B). Data are means±SD of three samples.

Release of surface adsorbed BMP-2 in the cell culture medium was also measured either directly by quantifying the amount in solution using an Elisa assay (FIG. 6) or by measuring the BMP-2 remaining in the film by microfluorimetry (data not shown). This was achieved in the absence and in the presence of cells to determine whether the presence of media containing 10% serum and/or cells were able to induce BMP-2 release. Noticeably, the released amounts in the medium were low, from ~2 to 25 ng/mL (FIG. 6A) and even lower, below 8 ng/mL, when cells were cultured on the films (FIG. 6B). For all conditions tested, these low release amounts corresponded to less than 3% of the effective adsorbed material. Consistent with these findings, no significant loss of BMP-$2^{CF}$ fluorescence was measured by microfluorimetry.

1.5. BMP-2 Induced Myoblast Differentiation in Osteoblasts

Figure 7:
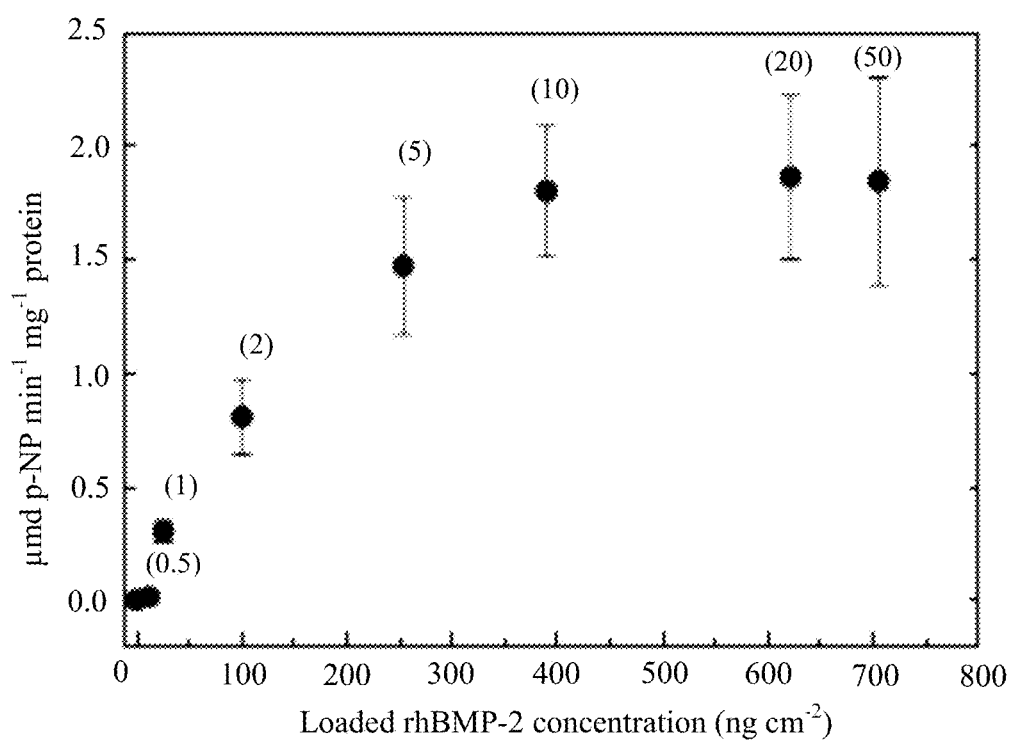
FIG. 7. Alkaline phosphatase activity of C2C12 cells seeded on BMP-2 loaded (PLL/HA)$_{12}$ films as a function of the loaded BMP-2 concentration (the initial BMP-2 concentration in solution is indicated in parenthesis above each data point). ALP was measured for cells cultured four days (one day in GM followed by 3 days in DM) in 24-well plates. Data are means±SD of three samples.
Figure 8:
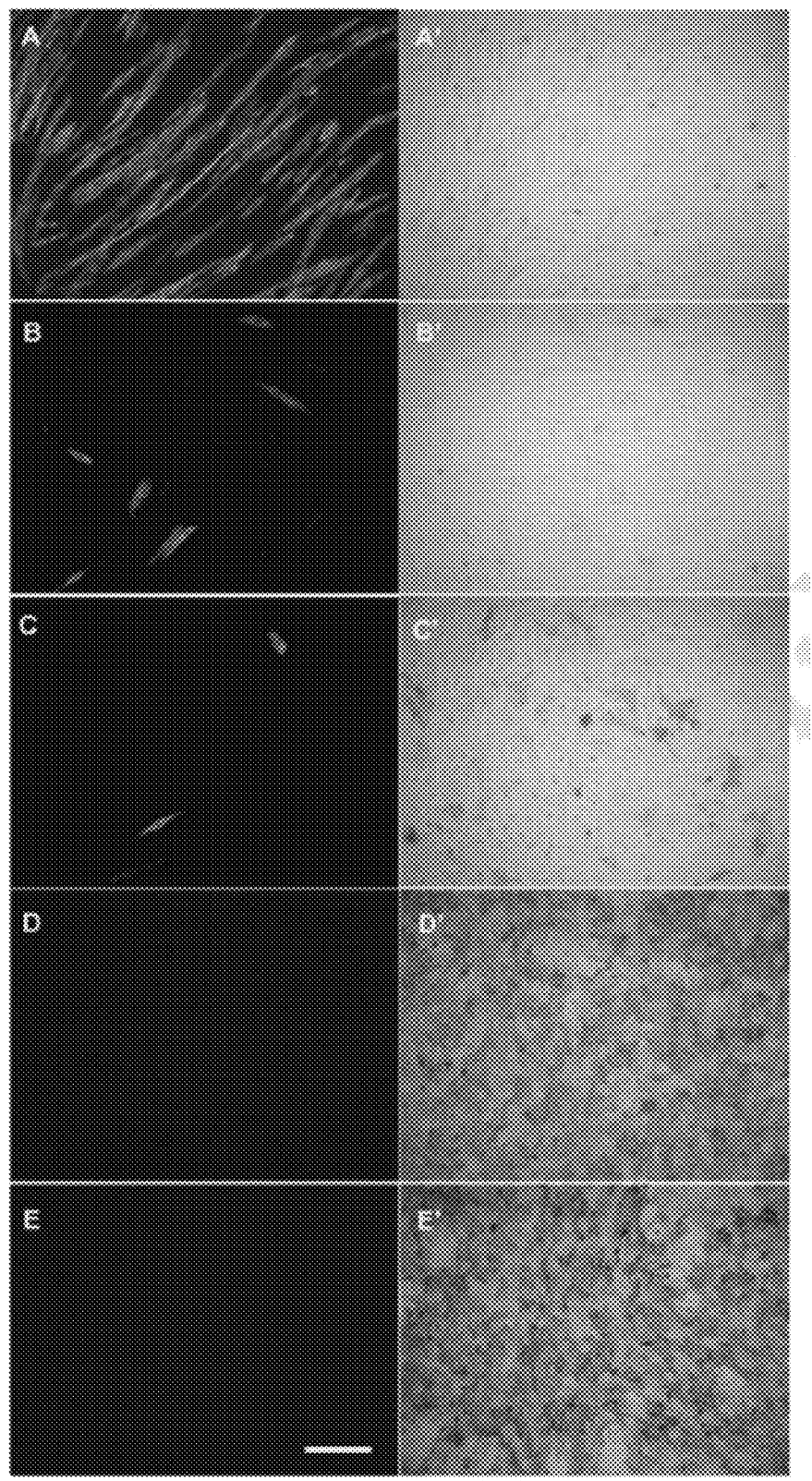
FIGS. 8A-8E. Immunochemical and histochemical staining of troponin T (A-E) and ALP (A'-E') of C2C12 on BMP-2 loaded films for increasing BMP-2 initial concentrations: (A) 0; (B) 0.5 µg/mL; (C) 1 µg/mL; (D) 10 µg/mL, (E) 50 µg/mL (scale bar 150 µm).

C2C12 myoblasts cells normally differentiate into myotubes when cultured in a low serum containing medium (differentiation medium, DM) on tissue culture polystyrene but can also differentiate into osteoblasts in the presence of BMP-2 in the culture medium. On cross-linked films without BMP-2, it was verified that cell differentiation into myotubes occurs effectively. Then, the bioactivity of film-adsorbed BMP-2 was measured by quantifying the alkaline phosphatase activity (ALP), an early marker of the osteogenic phenotype (FIG. 7). A control dose response curve was established for BMP-2 added in the culture medium (1 day in growth medium, GM, followed by 3 days in DM) (FIG. 13) and the same sequence of medium changes were kept for the film experiments, except that BMP-2 was substrate-adsorbed and not in solution. It was observed that ALP production increases as the amount of loaded BMP-2 (expressed here as a surface concentration) was increased saturating at ~400 ng/cm$^2$ BMP-2 (FIG. 7). Correlatively, the levels of Troponin T expression (a marker of myogenic differentiation) decreased (FIG. 8). On the control film (no BMP-2), cells differentiated in myotubes and expressed Troponin T (FIG. 8 A,A'). When the loading BMP-2 concentration was increased from 0.5 to 50 µg/mL, the cells progressively express more ALP (FIG. 8 B'-E'). It is worth noting that the cell differentiation program is significantly altered for BMP-2 initial concentrations as low as 0.5 µg/mL (corresponding to a loaded amount of 12 ng/cm$^2$) (FIG. 8 B-E). Thus, low doses of surface adsorbed BMP-2 can block C2C12 differentiation into myotubes and significantly higher doses (10 µg/mL BMP-2 loading solution corresponding to ~400 ng/cm$^2$ BMP-2 loaded) allow the development of an osteogenic phenotype as measured by ALP production. It was also checked that the ALP of cells cultured on the unfunctionalized films was null (FIG. 7). Interestingly, after 9 days of culture on BMP-2 loaded films (650 ng/cm$^2$), C2C12 cells began to aggregate and formed "nodules". These nodules resemble those formed by bone derived cell cultures that have the potential to mineralize in the presence of the appropriate minerals, forming structure close to bone in vivo (data not shown).

1.6. Long lasting Film Bioactivity over Several Cell Culture Cycles

Figure 9:
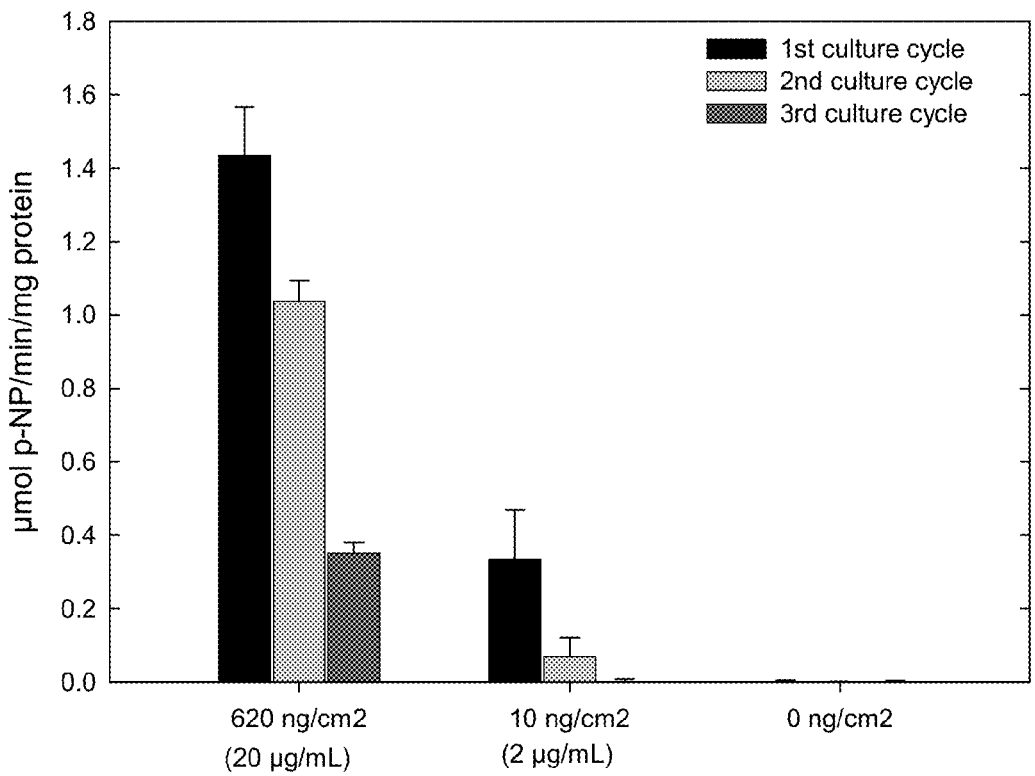
FIG. 9. Alkaline phosphatase activity of C2C12 cultured on BMP-2 loaded (PLL/HA)$_{12}$ films for three successive culture sequences (1 day in GM followed by 3 days in DM), the cells being detached between each culture sequence. Initial adsorbed BMP-2 amounts were 620 ng/cm$^2$ and 20 ng/cm$^2$ (corresponding to initial BMP-2 concentrations in solution of respectively 20 µg/mL and 2 µg/mL, as indicated in parenthesis). The control was a cross-linked (PLL/HA)$_{12}$ film without BMP-2 loaded. The raw activities represented for the different culture sequences and initial BMP-2 concentrations.

The persistence of surface adsorbed BMP-2 bioactivity is a key issue, as BMP-2 in solution is known to be rapidly degraded in few hours (B. Zhao, T. Katagiri, H. Toyoda, T. Takada, T. Yanai, T. Fukuda, U. I. Chung, T. Koike, K. Takaoka, R. Kamijo. J. Biol. Chem. 2006, 281, 23246-23253). BMP-2 functionalized films loaded at two BMP-2 concentrations were thus tested for their ability to retain BMP-2 activity over time. Three cell plating/replating culture sequences were performed one after the other on the same BMP-2 loaded films every four days after cells were gently detached. The ALP activity was measured 4 days after (re) plating at the end of each culture sequence. After a first sequence of culture, the film supported at least two additional cell culture sequences and still triggered induction of ALP albeit to a lower extent (FIG. 9). Films loaded at high initial BMP-2 concentration (20 µg/mL) are more efficient in keeping their bioactivity than films loaded at low concentration (2 µg/mL). This demonstrates that film can remain bioactive for at least 12 days in cell culture medium in contact with cells and that longer culture periods could be considered by simply increasing the amount of BMP-2 loaded in the film.

This also demonstrates the resistance of the BMP-2 loaded films toward cell traction forces during migration and differentiation as well as toward enzymatic secretions. To this respect, the (PLL/HA) thin film reservoir can be seen as a biomimetic system for BMP-2 delivery, increasing its local concentration and its life time through binding with the film. One of the film components, hyaluronan is indeed present in many extracellular matrices.

1.7. Mechanism of Action of Surface Adsorbed BMP-2

Figure 13:
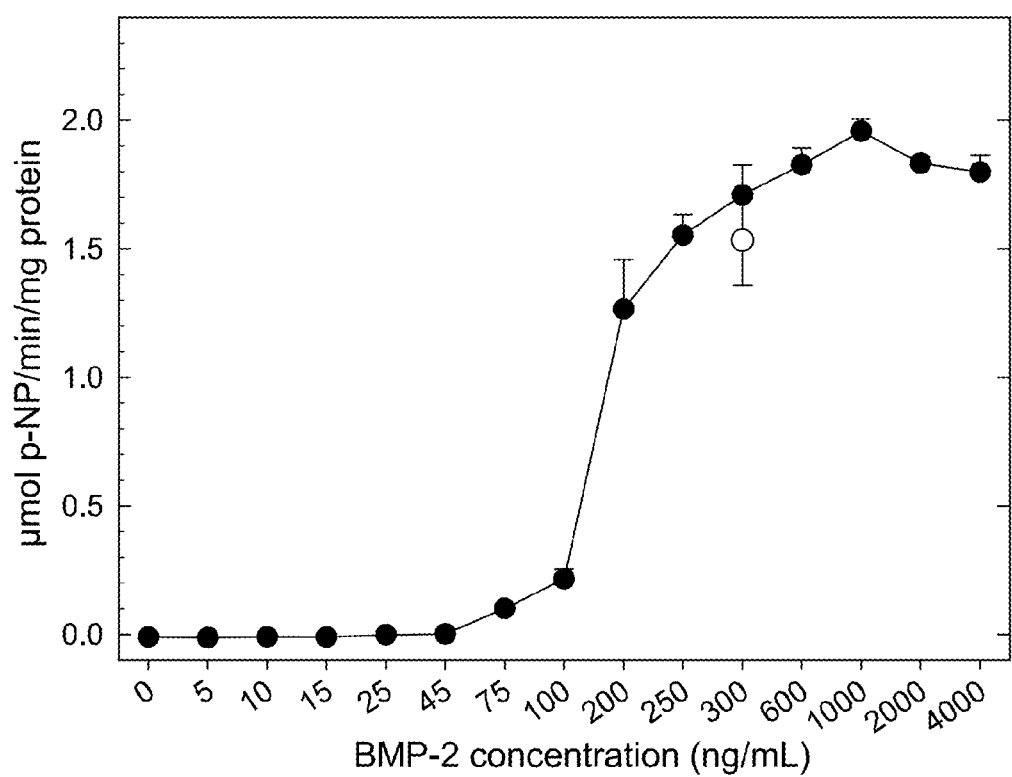
FIG. 13. (A) Dose response curve for ALP to increasing amounts of BMP-2 added in the cell culture medium. C2C12 were cultured 4 days, with medium and BMP-2 refreshment after day 1. BMP-2$^{CF}$ exhibited a similar activity as unlabeled BMP-2 (○).
Figure 14:
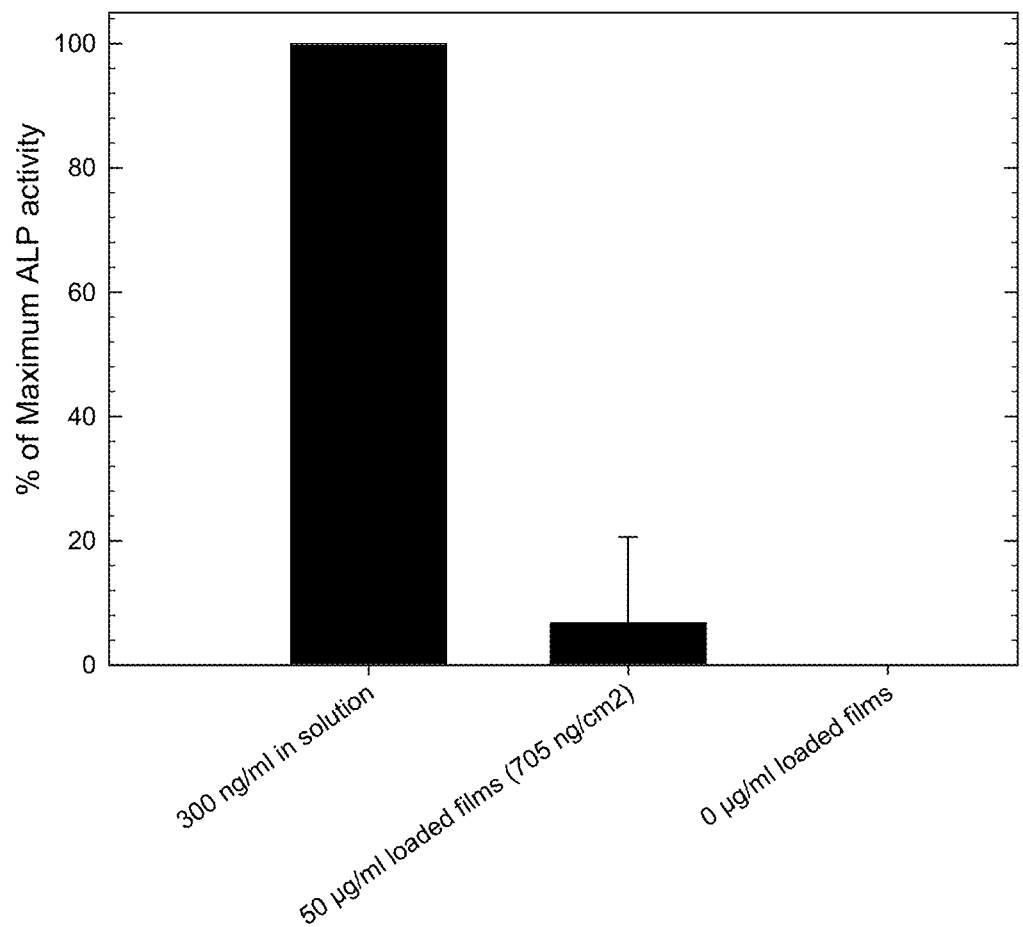
FIG. 14. ALP activity of C2C12 seeded in Transwell inserts in the presence of a BMP-2 loaded film on the bottom of the well. Reference ALP activity is given by C2C12 seeded on a Transwell insert with 300 ng/mL BMP-2 added to the culture media.
Figure 15A:
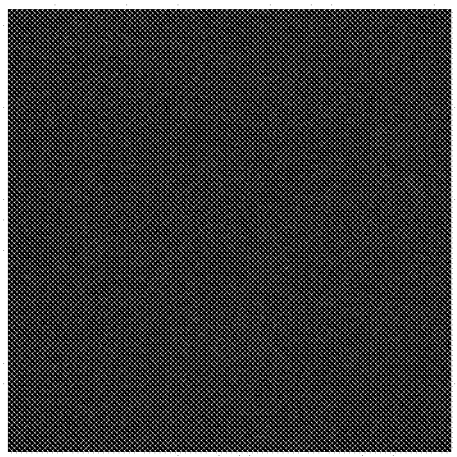
FIGS. 15A-15D. Confocal images of a BMP-2$^{Rhod}$ loaded cross-linked (PLL/HA)$_{24}$-PLL$^{FITC}$-HA film after contact with cells in culture medium for 4 days. Top views of the film (A) in the red channel (BMP-2$^{rhodamine}$) and (B) in the green channel (PLL$^{FITC}$) (image size are 35.7 µm×35.7 µm). (C) Vertical section of the film (C) (white line is 4.2 µm) and (D) corresponding intensity profile. The films are not altered by the cells and no significant additional diffusion of BMP-2 within the film is visible after 4 days.
Figure 15B:
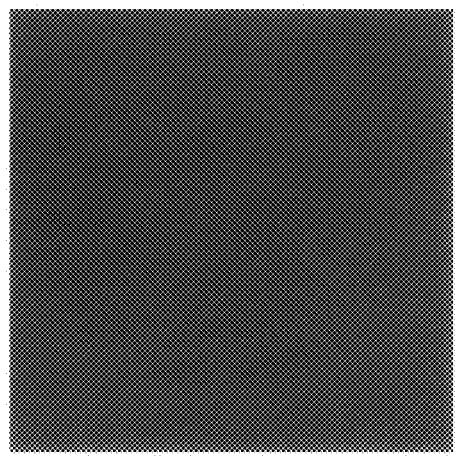
Figure 15C:
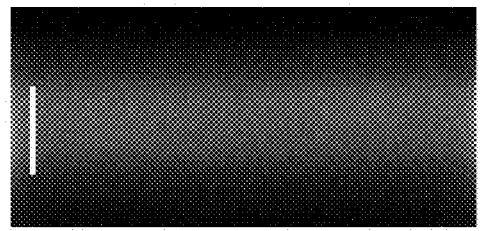
Figure 15D:
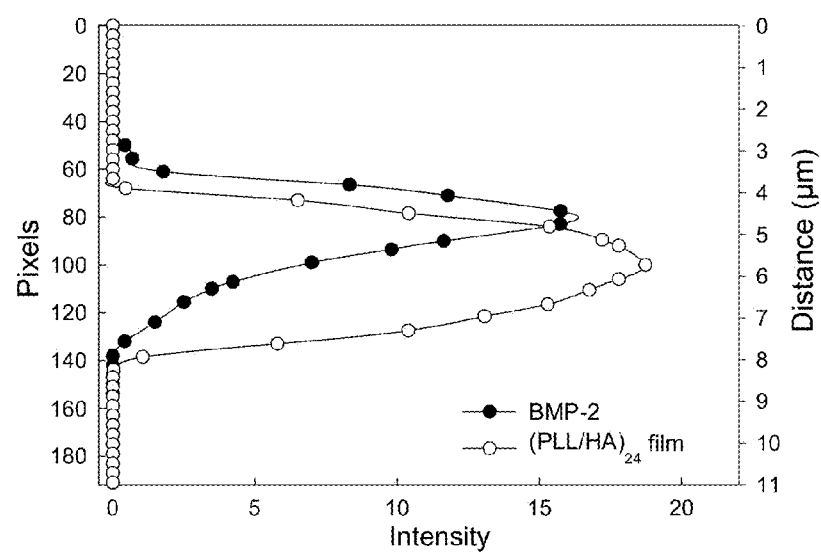

The results show that BMP-2 adsorbed in LbL films retains its bioactivity. In fact, it seems more generally that LbL films are compatible with the biological activity of other embedded or adsorbed proteins. In addition, the results demonstrate that active BMP-2 is extremely weakly released in the medium, and that the release was even lower in the presence of cells (FIG. 5). One could argue that some inactive (or degraded) BMP-2 (and therefore not detected) might be released from the film, but this is in contradiction with the observation that ~95% of the initial fluorescence of BMP$^{CF}$ remains in the film. Importantly, it was verified that doses of BMP-2 similar to those released from the films could not induce ALP production (FIG. 13). A further check that the negligible amount of BMP-2 released in the medium was not responsible for the induced bioactivity was obtained from Transwell experiments. In these tests, cells were cultured in Transwell inserts without direct contact with the film surface, the BMP-2 loaded films being introduced at the bottom of the well. For a highly loaded film (initial BMP-2 concentration 50 µg/mL, ~700 ng/cm$^2$), only a weak expression of ALP was measured (FIG. 14). In addition, it was observed the films by CLSM after the cells were cultured on top of them for 4 days and no film degradation could be evidenced at this resolution (FIG. 15). Thus, these results strongly support the hypothesis that cells come into contact with the films and "sense" the immobilized BMP-2 without degrading the film or the BMP-2, although an extremely localized degradation beneath the cells by cell enzymes such as metallo-proteases and hyaluronidases cannot be excluded.

For BMP-2, the cascade of events leading to signal transduction has been described (W. Sebald, J. Nickel, J. L. Zhang, T. D. Mueller. *Biol. Chem.* 2004, 385, 697-710). Receptor signaling occurs through the hetero-oligomerization of two types of receptor chains (BMPRs), BMPR I and BMPRII upon BMP-2 binding. The ligand binds to the extracellular domain of BMPR I which is then confined to the membrane surface. BMPR II chains are then recruited until the final hetero-oligomer signaling complex is formed. In the present case, the surface bond (immobilized) BMP-2 may thus favor the direct contact with the receptor chains by restricting their diffusion and/or internalization.

2. Conclusions

These results provide evidence that films of the invention can be used as a tunable reservoir for BMP-2 delivery to cells, BMP-2 being trapped in the film and remaining bioactive for more than 10 days. The optimal loading conditions were defined and the loaded amount was tuned by varying both initial BMP-2 solution concentration and film thickness. Substrate-adsorbed BMP-2 was bioactive and induced myoblast differentiation into osteoblasts in a dose-dependent manner. In addition, film bioactivity was persistent over three successive culture cycles. This type of coating combines the ease of construction by dip coating and the localized delivery of bioactive growth factors. These results should have an important impact on the development of biofunctionalized surfaces for tissue engineered constructs or for metallic implants. Indeed, as (PLL/HA) films were recently successfully deposited on polyelectrolyte terephtalate prosthesis and onto nickel-titanium implant surfaces, the coated surfaces of the invention can be biomaterial surfaces for providing BMP-2 effects in vivo.

Figure 16:
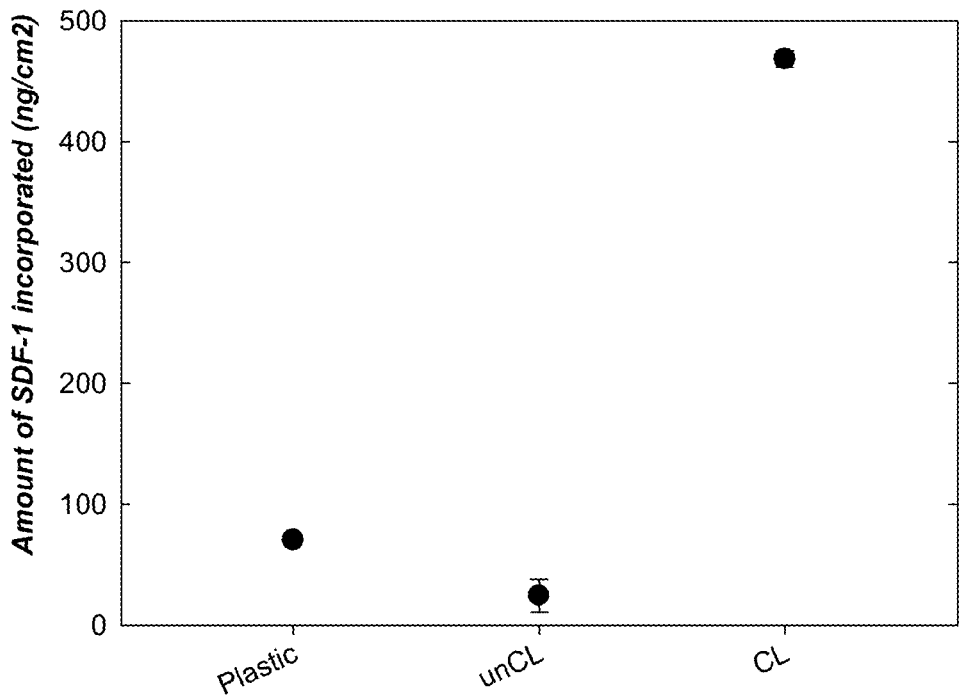
FIG. 16. Amount of cytokine SDF-1 loaded in cross-linked (PLL/HA)$_{12}$ films (CL) compared to a control surface (tissue culture polystyrene, i.e., plastic) and an uncrosslinked PLL/HA film (unCL).

3. Additional Experiments 3.1 Incorporation of SDF-1 Growth Factor in a PLL/HA Film The recombinant growth factor SDF-1 labelled with tetramethylrhodamine (TR) was loaded into cross-linked (PLL/HA)$_{12}$ films. The amount remaining after 12 washing steps (at 30 min from each other) is plotted for the different conditions: control tissue culture polystyrene (plastic), native (uncrosslinked film) and film cross-linked following our protocol. Result is presented on FIG. 16.

The amount of SDF-1 loaded in cross-linked films is 6.7 times higher than on the control surface. These results prove that films synthesised according to the invention may be used as biomimetic reservoirs for the storage and release of different proteins, including BMP-2 and SDF-1.

3.2 Incorporation of BMP-2 in a PLL/HA-HEP Film

Following the same protocol as for PLL/HA films, different blend films were loaded by post-diffusion of a solution of fluorescently labeled rhBMP-2 at various concentrations. The incorporated amounts were estimated by measuring the fluorescence of the films.

Figure 17:
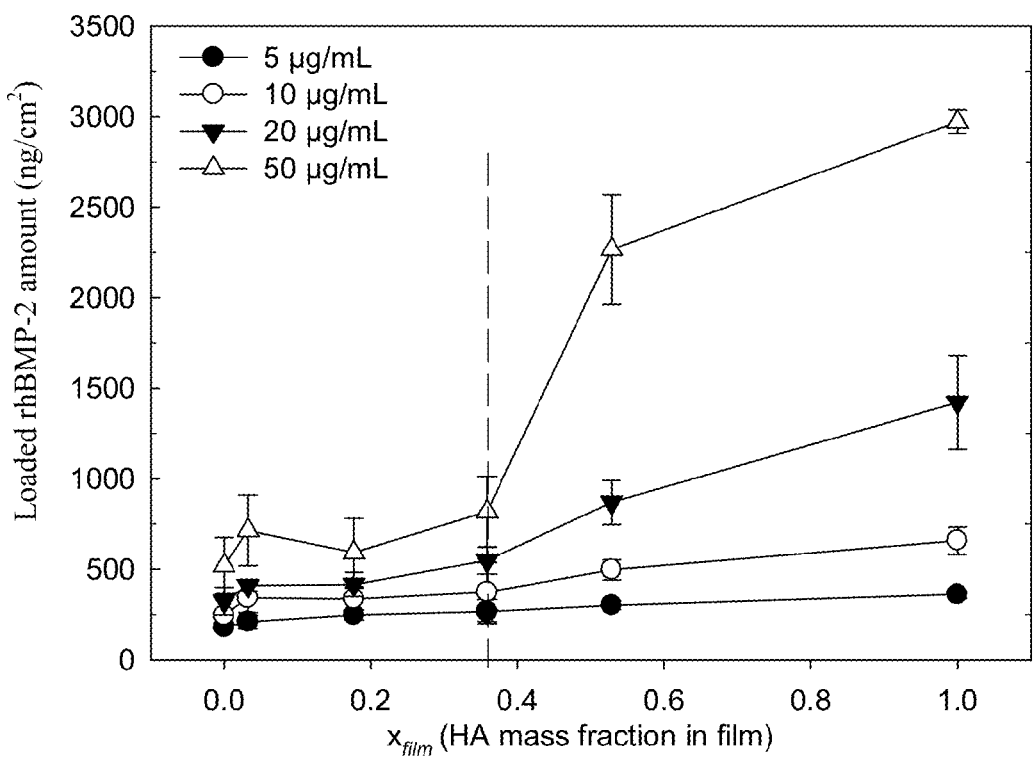
FIG. 17. Effective loaded amounts of rhBMP-2 in the films as a function of the HA mass fraction in the film, $x_{film}$, for different rhBMP-2 concentrations in the initial solution.

The effective loaded amounts of rhBMP-2 in PLL/HA-HEP films as a function of the HA mass fraction in the film for different rhBMP-2 concentrations in the initial solution are represented in FIG. 17.

3.3 Deposition of Films onto Various Materials

Figure 18:
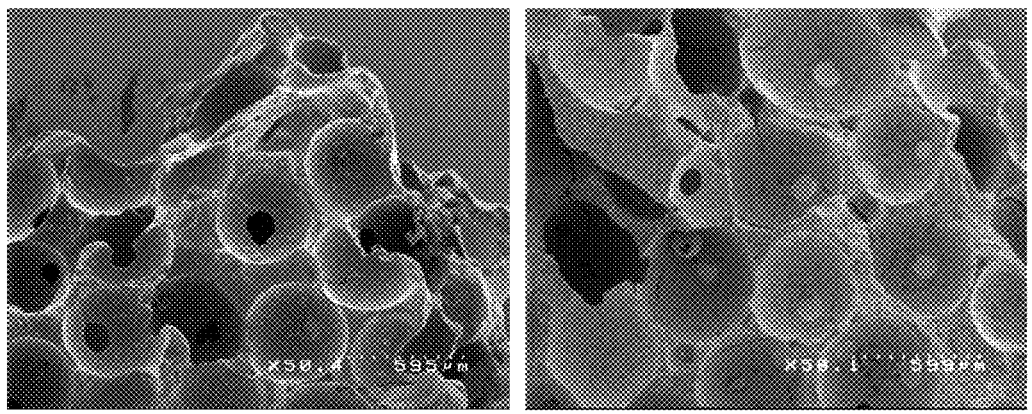
FIG. 18. Low magnification SEM pictures of a porous bone filling material (TCP/HAP composite) uncoated (left) or coated (right) with a (PLL/HA) cross-linked film.

Films made of (PLL/HA) of 12 or 24 layer pairs were first deposited on various types of bone filling materials currently used for orthopaedic applications. These materials differ from another, mostly with regards to their chemical composition, porosity and mechanical properties. The deposition of the polyelectrolyte multilayer films were thus characterized on several of these materials, made from hydroxyhapatite (HAP) and/or Tricalcium phosphate (TCP): BCP BiCalPhos from Medtronics, TRIHA+ from Teknimed. Deposition of the film was evidenced by Scanning Electron Microscopy. The surface roughness was smoothened by the presence of the film. The film was shown to deposit on all tested materials, both porous and non-porous. SEM pictures of the deposited films are provided in FIG. 18.

Figure 19:
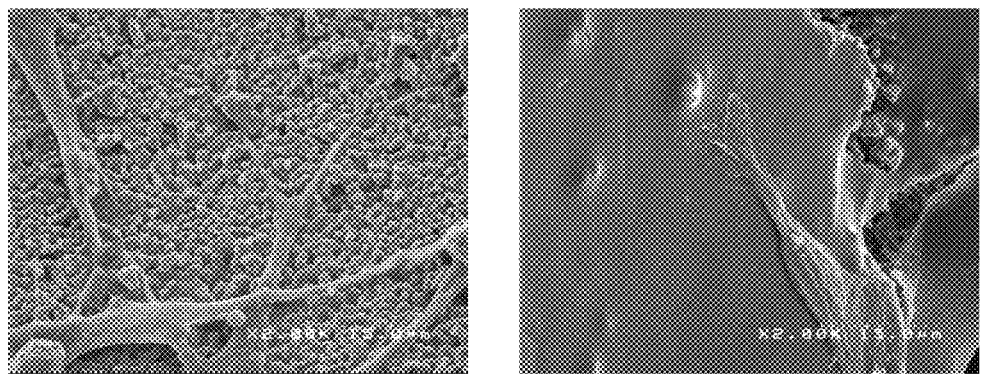
FIG. 19. SEM pictures of a bone substitute (TCP/HAP composite) covered with (PLL/HA)$_{24}$ and seeded with C2C12 cells.

The C2C12 muscle cell adhesion was also observed by SEM for cells grown on either bare biomaterials (TCP/HAP composite) or biomaterials coated with the bioactive film cross-linked (PLL/HA)$_{24}$ film loaded with rhBMP-2. Cell adhesion on the film coated bone biomaterials was very good. SEM pictures of the biomaterial covered with the film and seeded with C2C12 cells are provided in FIG. 19.

Figure 20:
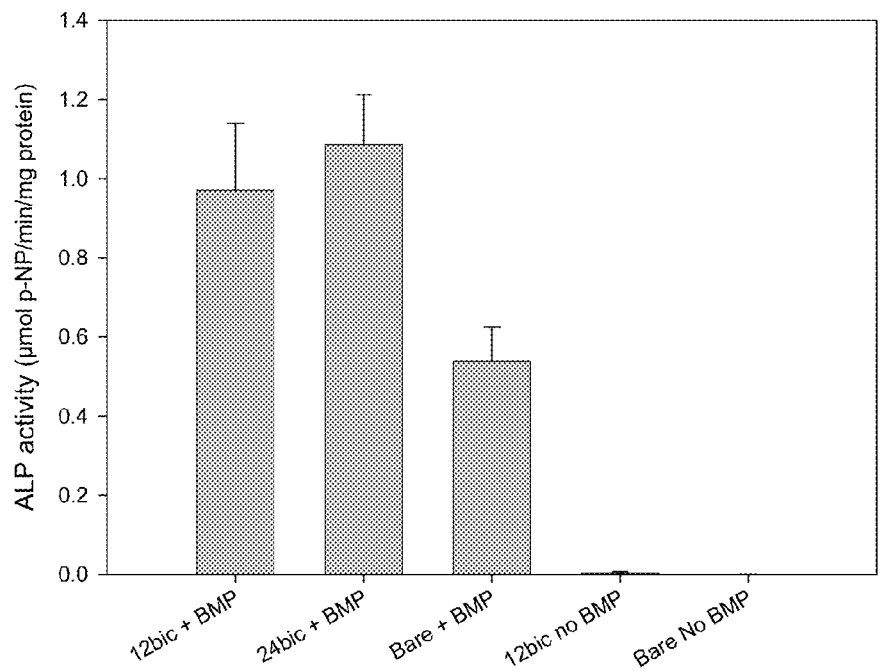
FIG. 20. Representation of alkaline phosphatase expression in cells cultured on a cross-linked (PLL/HA) film loaded with rhBMP-2 deposited on TCP/HAP composite compared to cells cultured in the biomaterials with BMP-2 added in the medium.

Alkaline phosphatase (ALP) activity was also measured for C2C12 cells grown in to porous biomaterials for 4 days. Results are provided on FIG. 20. The expression of ALP is significantly higher when the cells are cultured on a cross-linked (PLL/HA) film loaded with rhBMP-2 (film deposited on the porous biomaterial) than in the biomaterials with BMP-2 added in the medium.

Figure 21:
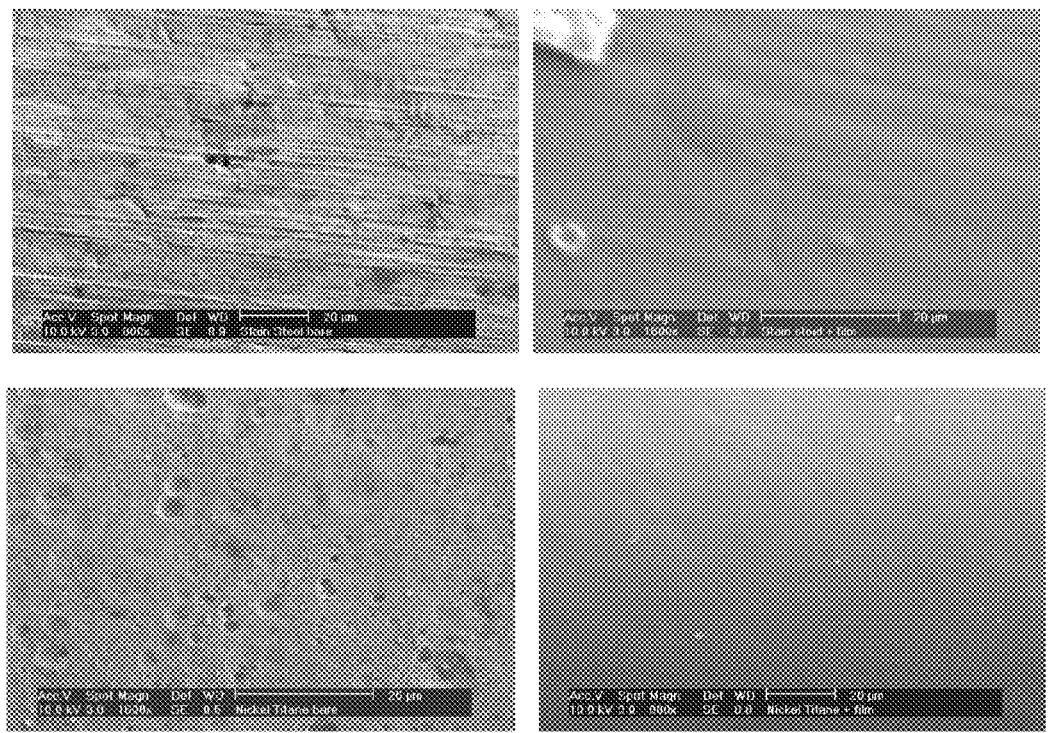
FIG. 21. SEM pictures of a stainless steel sample: bare (top left) or coated with a cross-linked (PLL/HA)$_{24}$ film (top right) and of a nickel titanium sample: bare (bottom left) or coated with a cross-linked (PLL/HA)$_{24}$ film (bottom right).

(PLL/HA) films were additionally shown to deposit onto nickel titanium and stainless steel. SEM pictures of the deposited films are provided in FIG. 21.

3.4 Conclusions

These results show that, on the first hand, films prepared according to the process of the invention can be used as biomimetic reservoirs for various biological molecules. In addition, films prepared according to the process of the invention can incorporate these molecules in a large amount.

They additionally prove that loading of biomolecules may be performed efficiently in various types of films prepared according to the process of the invention.

They finally demonstrate that films prepared according to the process of the invention may be deposited onto various types of materials.

4. Experimental Section

4.1. Film Preparation and Cross-linking Procedure

4.1.1 PLL/HA Film

HA (sodium hyaluronate, $2\times10^5$ g/mol) was purchased from Medipol (Switzerland) and PLL ($2\times10^4$ g/mol) was purchased from Sigma (France). PLL (0.5 mg/mL) and HA (1 mg/mL) were dissolved in a Hepes-NaCl buffer (20 mM Hepes, 0.15 M NaCl, pH 7.4). For all cellular experiments, the films were prepared as previously described[31] with a dipping machine (Dipping Robot DR3, Kierstein GmbH, Germany) on 14 mm diameter glass slides (VWR Scientific, France). For BMP-2 integration and release experiments, films were manually constructed in 96 well plates (Nunc, Denmark) starting with a first layer of poly(ethyleneimine) ($7\times10^4$ g/mol, Sigma, France) at 5 mg/mL. Briefly, 50 µL of polyelectrolyte solutions were deposited in each wells, let to adsorb for 8 minutes, before being washed two times with 70 µL of rinsing solution (0.15 M NaCl, pH~6) for 1 min. The sequence was repeated until the buildup of a $(PLL/HA)_i$, i being the number of layer pairs, was achieved.

Films were cross-linked following the protocol previously described[31] using 1-Ethyl-3-(3-Dimethylamino-propyl) Carbodiimide (EDC) at 50 mg/mL and N-Hydrosulfosuccinimide (sulfo-NHS) at 11 mg/mL (both purchased from Sigma, France). After introduction of the coated glass slides in the culture plates, 0.5 mL of cross-linking solution was deposited in each well for 24-well plates (respectively 0.12 mL for 96-well plates) and left for 18 h at 4° C. Final washing was performed with 0.15 M NaCl at pH 8 for 1 h. This cross-linking condition was chosen to ensure that C2C12 cells adhere, proliferate and differentiate optimally onto the films that do not contain BMP-2. [44]

4.1.2 PLL/HA-HEP Film

Hyaluronan (HA, 360 kDa, Lifecore, MW of the monomeric unit 378 g/mol) and heparin (HEP, H4784, 15 kDa Sigma, Saint-Quentin Fallavier, France, MW of the monomeric unit 494 g/mol) were dissolved at 1 mg/mL in a Hepes-NaCl buffer (20 mM Hepes, 0.15 M NaCl, pH 7.4) in water or in 0.15 M NaCl in $D_2O$ adjusted at pH 7.4 for the FTIR experiments. HA is a polyanionic macromolecules (1 carboxylic group/disaccharide unit) with a pKa~2.9. HEP (one carboxylic group and 2 to 3 sulfate groups per disaccharide unit) is a strong polyelectrolyte. Mixture of HA and HEP solution were realized before film buildup at various mass ratios (designated as $x_{sol}$). Poly(L-lysine) (PLL, Sigma, P2626, lot number 027KS102) was prepared at 0.5 mg/mL in the same buffer. During film buildup, all the rinsing steps were performed with the salt containing solution and films were never dried.

For rhBMP-2 integration and release experiments, films were manually constructed in 96 well plates (Nunc, Denmark) starting with a first layer of poly(ethyleneimine) ($7\times10^4$ g/mol, Sigma, France) at 5 mg/mL. Briefly, 50 µL of polyelectrolyte solutions were deposited in each wells, let to adsorb for 8 minutes, before being washed two times with 70 µL of rinsing solution (0.15 M NaCl, pH~6) for 1 min. The sequence was repeated until the buildup of a $(PLL/HA)_i$, i being the number of layer pairs, was achieved.

Films were cross-linked as previously described using a 30 mg/mL solution of 1-Ethyl-3-(3-dimethylaminopropyl)carbodiimide hydrochloride (EDC) mixed with a 11 mg/mL solution of N-hydroxysulfosuccinimide (sulfo-NHS).

4.2. BMP-2 Labeling

BMP-2 (Clinical Grade, Wyeth BioPharma, USA) was dissolved at 0.3 mg/mL in 4 mM HCl and frozen at −20° C. until use. For fluorescent labeling, the pH of the protein was raised to 8 with a bicarbonate buffer (50 mM). BMP-2 was reacted for 4 hrs at room temperature with 1:20 (mol/mol) of 5(6)-Carboxyfluorescein-N-hydroxysuccinimide ester (CF, Boehringer, Mannheim, Germany), or 1:100 (mol/mol) tetramethylrhodamine isothiocyanate (Rhod, Aldrish, Milwaukee, Wis.), before being re-acidified with acetate buffer (0.2 M, pH~3). The labeled protein ($BMP\text{-}2^{CF}$ and $BMP\text{-}2^{Rhod}$) was separated from the reagents using a Sephadex G25 column (GE Heathcare, France) eluted with 1 mM HCl. The molar grafting ratios were estimated by determining the respective molar concentration of dye and of protein and calculating the grafting ratio (11±2%).

Gel Electrophoresis.

Respectively 3 µg and 4.5 µg of BMP-2 and $BMP\text{-}2^{CF}$ samples were mixed with Laemmli buffer (LB), loaded on a 20% polyacrylamide gels and then stained using Coomassie blue. The two BMP-2 chains were dissociated in reducing conditions by adding dithiothreitol (DTT) containing LB to the protein.

4.3. Quantification of BMP-2 and Confocal Observations

Incorporation and initial release studies were performed on $(PLL/HA)_i$, (i=12, 18, 24) films constructed in 96-well plates. The films were always pre-equilibrated for 30 min in the medium in which BMP-2 was suspended (either HCl 1 mM, or Hepes 20 mM, pH 7.4, with or without added NaCl). 50 µL of $BMP\text{-}2^{CF}$ at increasing concentrations (from 0.5 to 150 µg/mL) were deposited onto the films and let adsorbed overnight at 4° C. 150 µL of Hepes-NaCl were then added in each well and let at room temperature for 15 min. The solution was then removed and replaced by fresh Hepes-NaCl buffer (pH 7.4) before measuring fluorescence (Ex485/Em535) using a Twinkle LB970 microfluorometer (Berthold, Germany). For release studies, the wells were washed with the Hepes-NaCl solution (pH 7.4) and the fluorescence measured at various time intervals. The incorporated amount was calculated based on a calibration curve obtained with known amounts of BMP-2 in solution. BMP-2 loading on film coated glass slides for cell culture studies were achieved in a similar way. Coated slides were washed for 7 h in Hepes-NaCl before being sterilized 15 min under UV light. For BMP-2 incorporation, the adsorbed amounts are expressed in $ng/cm^2$ for ease of comparison, even though the films have a small roughness of 7 nm. The amounts of BMP-2 released in the culture medium (GM, 10% serum) were determined using the Quantikine BMP-2 immunoassay (R&D Systems, France) according to the manufacturer's instructions. Experiments have been performed at least in triplicate, with three independent samples per condition in each experiment.

Film topography and vertical structure were imaged using a LSM 510 META confocal microscope (Carl Zeiss, Germany) for films on 14 mm glass slides as previously described[40]. For BMP-2 deposition, the procedure described above was followed except that the deposited volume was larger (0.3 mL of $BMP\text{-}2^{Rhod}$).

4.4. Size Exclusion Chromatography

BMP-2$^{CF}$ (MW~27 kDa) or a mixture of BMP-2$^{CF}$ and HA (MW~200 kDa) at a molar ratio of ~1/10 were suspended in 1 mM HCl or 40 mM Tris (pH 7.4) at room temperature and left 1 h before being injected on a Superdex 75 size exclusion column (GE Healthcare, UK) with a size exclusion at 100 kDa. The protein was eluded with HCl 1 mM or 40 mM tris (pH 7.4) at a flow rate of 1 mL/min and fractions of 0.5 mL were collected and neutralized with 50 μL of 400 mM Hepes (pH 7.4) if needed. The fluorescence (Excitation 485/Emission 535) of each fraction was then measured by microfluorimetry to generate an elution profile.

4.5 C2C12 Culture

C2C12 cells (<20 passages) were maintained in polystyrene flasks in a 37° C., 5% $CO_2$ incubator, and cultured in a 1:1 Dulbecco's Modified Eagle Medium (DMEM)/F12 medium (Gibco, Invitrogen, Cergy-Pontoise, France) supplemented with 10% fetal bovine serum (FBS, PAA Laboratories, Les Mureaux, France), containing 10 U/mL penicillin G and 10 μg/mL streptomycin (Gibco, Invitrogen, Cergy-Pontoise, France) (growth medium, GM). Cells were subcultured prior to reaching 60-70% confluence (approximately every 2 days). For all experiments, C2C12 cells seeded on films at $4.5 \times 10^4$ cells/cm$^2$ in growth medium (GM) were allowed to grow for one day and were then switched to the differentiation medium (DM) composed of 1:1 DMEM/F12 supplemented with 2% horse serum (HS, PAA Laboratories, Les Mureaux, France), containing 10 U/mL penicillin G and 10 μg/mL streptomycin, for 3 days.

To test C2C12 differentiation by medium released BMP-2, 3000 cells were seeded in the upper compartment of Transwell inserts (6.5 mm diameter, 0.4 μm pore membrane, Costar, Cambridge, Mass.) and BMP-2 loaded films were placed at the bottom of the wells (in 24 well plates), avoiding direct contact of the cells with the film. Control cultures were done with media supplemented with 300 ng/ml BMP-2 (without films) and with unfunctionalized films.

4.6 Film Bioactivity: Alkaline Phosphatase Assay

After 4 days in culture on BMP-2 loaded films, C2C12 cells were assayed for alkaline phosphatase activity (ALP), a marker for osteoblast differentiation. After removal of culture medium, cells were lysed by adding 0.5 mL of 0.1% Triton-X100 in PBS and sonicated. A buffer containing 0.1 M 2-amino-2-methyl-1-propanol (Sigma, St Quentin-Fallavier, France), 1 mM $MgCl_2$, 9 mM p-nitrophenyl phosphate (pNPP) (Euromedex, Mundolsheim, France), adjusted to pH 10 with HCl was used to assay the cell lysate for ALP. Reaction was followed over 5 min in a 96-well plate by measuring the absorbance at 405 nm using a Multiskan EX plate reader (Labsystem, Helsinki, Finland). The activity was expressed as μmoles of p-nitrophenol produced per minute per mg of protein. Total protein contents of the samples were determined using a BCA protein assay kit (Interchim, Montlucon, France). Experiments have been performed in triplicate, with three independent samples per condition in each experiment.

To assess the ability of BMP-2 loaded films to retain their bioactivity in long term cell culture, the BMP-2 loaded films were seeded with cells and followed a standard cell culture sequence (1 day in GM, 3 days in DM). Cells were then rinsed with PBS without calcium nor magnesium and were gently detached with 2 mM EGTA in PBS added at 4° C. (without trypsin). A gentle flux was applied by pipetting to proceed to cell detachment, while care was taken to avoid scratching the film. Films were then rinsed, sterilized by UV, and re-seeded. After three culture sequences, ALP activities were measured as described above.

4.7. Troponin-T and Alkaline Phosphatase Histochemical Analyses

Cells were fixed with 3.7% formaldehyde for 20 min, then permeabilized in 0.2% Triton X-100 for 4 min. As a marker for myogenic differentiation, cells were labeled with monoclonal mouse anti-troponin T (1:100) (Sigma, St Quentin-Fallavier, France). Primary antibodies were revealed using Alexa Fluor 488 conjugated goat anti-mouse (1:1000, Molecular Probes-Invitrogen, France). Alkaline phosphatase, as a marker for osteodifferentiation, was stained using fast blue BB salt. Briefly, a mixture of 0.1 mg/ml naphthol (Fluka, Gillingham, UK) in DMF, 2 mM $MgCl_2$ and 0.6 mg/mL fast blue BB salt (Fluka, Gillingham, UK) was deposited on the cells until coloration appeared. Observation of the stained cells was performed using a binocular microscope (Carl Zeiss SAS, Stemi SV11) or an Axiovert 200M microscope (Carl Zeiss SAS, Le Pecq, France) using a 10× objective.

All experiments were repeated at least 3 times. Error bars represent standard deviations.

The invention claimed is:

1. An article coated by a process for coating a surface, said process comprising the following steps:
    (a) sequentially depositing on a surface at least one layer of alternate adsorbed polyelectrolytes to provide a coated surface presenting complementary amino and carboxylic reactive groups, wherein a first (or conversely second) polyelectrolyte is a cationic polymer comprising said amino groups and a second (or conversely first) polyelectrolyte is an anionic polymer comprising said carboxylic groups,
    (b) reacting said complementary reactive groups of the coated surface in the presence of a coupling agent, as to form amide bonds between said complementary reactive groups giving rise to a cross-linked polyelectrolyte multilayer film having a thickness ranain from 500 nm to 20 micron, and
    (c) treating said cross-linked polyelectrolyte multilayer film with a protein containing solution as to incorporate said protein on and inside said cross-linked polyelectrolyte multilayer film.

2. The coated article according to claim 1, wherein the article is selected from the group consisting of blood vessel stents, angioplasty balloons, vascular graft tubing, prosthetic blood vessels, vascular shunts, heart valves, artificial heart components, pacemakers, pacemaker electrodes, pacemaker leads, ventricular assist devices, contact lenses, intraocular lenses, sponges for tissue engineering, foams for tissue engineering, matrices for tissue engineering, scaffolds for tissue engineering, biomedical membranes, dialysis membranes, cell-encapsulating membranes, drug delivery reservoirs, drug delivery matrices, drug delivery pumps, catheters, tubing, cosmetic surgery prostheses, orthopaedic prostheses, dental prostheses, bone and dental implant, wound dressings, sutures, soft tissue repair meshes, percutaneous devices, diagnostic biosensors, cellular arrays, cellular networks, microfluidic devices, and protein arrays.

3. The coated article according to claim 1, wherein the article is a material used in orthopaedic surgery, an orthopaedic prosthesis, a bone graft or a bone substitute.

* * * * *